(12) United States Patent
Doyle

(10) Patent No.: US 9,764,481 B2
(45) Date of Patent: Sep. 19, 2017

(54) FLEXIBLE WRIST-TYPE ELEMENT

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 926 days.

(21) Appl. No.: 13/702,524

(22) PCT Filed: Oct. 8, 2010

(86) PCT No.: PCT/US2010/052056
§ 371 (c)(1),
(2), (4) Date: Feb. 28, 2013

(87) PCT Pub. No.: WO2011/155957
PCT Pub. Date: Dec. 15, 2011

(65) Prior Publication Data
US 2013/0263685 A1 Oct. 10, 2013

Related U.S. Application Data

(60) Provisional application No. 61/353,567, filed on Jun. 10, 2010.

(51) Int. Cl.
*B25J 17/02* (2006.01)
*B25J 9/10* (2006.01)
(Continued)

(52) U.S. Cl.
CPC ............ *B25J 17/02* (2013.01); *A61B 34/30* (2016.02); *B25J 9/106* (2013.01); *B25J 17/0241* (2013.01);
(Continued)

(58) Field of Classification Search
CPC .... B25J 17/02; B25J 17/0266; B25J 17/0258; B25J 17/0241; B25J 9/06; B25J 9/106;
(Continued)

(56) References Cited

U.S. PATENT DOCUMENTS 3,160,290 A * 12/1964 Wilson .................. B25J 9/14
414/4
4,511,305 A * 4/1985 Kawai ................ B25J 9/046
414/735

(Continued)

FOREIGN PATENT DOCUMENTS

WO WO 2009/158708 A1 12/2009

OTHER PUBLICATIONS

European Search Report and Written Opinion issued in European Patent Application No. EP10853025 mailed Mar. 21, 2017.

*Primary Examiner* — David M Fenstermacher
(74) *Attorney, Agent, or Firm* — Arent Fox LLP

(57) ABSTRACT

A flexible wrist-type element, comprising: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position, wherein a point of intersection between the second longitudinal axis and the first longitudinal axis moves during movement between the first position and the second position; a driver assembly moveably supported by the base housing and the operational housing; and wherein the driver assembly is configured to actuate the operational element relative to the operational housing.

27 Claims, 35 Drawing Sheets

(51) Int. Cl.
*A61B 34/30* (2016.01)
*A61B 17/00* (2006.01)

(52) U.S. Cl.
CPC ............... *A61B 2017/00477* (2013.01); *A61B 2017/00539* (2013.01); *A61B 2034/305* (2016.02); *Y10S 901/29* (2013.01); *Y10T 74/20335* (2015.01)

(58) Field of Classification Search
CPC ........ B25J 9/046; B25J 9/0072; B25J 9/0078; A61B 19/22; A61B 19/2203; A61B 18/1445; A61B 2017/00539; A61B 2017/2936
See application file for complete search history.

(56) References Cited

U.S. PATENT DOCUMENTS

| | | | | |
|---|---|---|---|---|
| 4,805,477 A | * | 2/1989 | Akeel | B25J 9/06 74/490.05 |
| 5,222,409 A | * | 6/1993 | Dalakian | B25J 9/046 414/733 |
| 5,697,256 A | * | 12/1997 | Matteo | B25J 9/104 475/210 |
| 6,902,560 B1 | | 6/2005 | Morley et al. | |
| 7,608,083 B2 | * | 10/2009 | Lee | A61B 34/20 606/1 |
| 8,677,854 B2 | * | 3/2014 | Lundberg | B25J 9/06 74/490.01 |
| 9,161,772 B2 | * | 10/2015 | Hyodo | B25J 13/02 |
| 2003/0109898 A1 | | 6/2003 | Schwarz et al. | |
| 2008/0196533 A1 | * | 8/2008 | Bergamasco | B25J 17/0266 74/490.06 |
| 2009/0171147 A1 | * | 7/2009 | Lee | A61B 17/29 600/104 |
| 2009/0299143 A1 | | 12/2009 | Conlon et al. | |
| 2009/0320637 A1 | | 12/2009 | Doyle et al. | |
| 2010/0229669 A1 | * | 9/2010 | Kim | B25J 9/106 74/490.01 |
| 2011/0196509 A1 | * | 8/2011 | Jansen | B25J 9/109 623/26 |

* cited by examiner

FLEXIBLE WRIST-TYPE ELEMENT

CROSS-REFERENCE TO RELATED APPLICATION

This application is a National Stage entry of International Application No. PCT/US2010/052056 filed Oct. 8, 2012, which claims priority to U.S. Provisional Patent Application No. 61/353,567 which was filed Jun. 10, 2010. This application is also related to Applicant's U.S. Provisional Patent Appl. No. 61/297,630 titled "HYDRAULIC DEVICE INCLUDING A SPOOL VALVE" filed on Jan. 22, 2010, U.S. Provisional Patent Appl. No. 61/297,784 titled, "OVERFORCE MECHANISM" filed on Jan. 27, 2010, U.S. Provisional Patent Appl. No. 61/237,042 titled "ARTICULATED SURGICAL TOOL" filed on Aug. 26, 2009 and U.S. Provisional Patent Appl. No. 61/354,042 titled "REDUCED BACKLASH JOINT AND METHOD OF MAKING SAME' filed on Jun. 11, 2012, entirety of each of which is hereby incorporated by reference herein.

BACKGROUND OF THE INVENTION

Field of the Invention

Aspects of the present invention relate to wrist elements employed in actuating devices.

Background of the Related Art

There is a need for mechanisms for transmitting mechanical force around corners and bends. In one example, these mechanisms are needed in surgical environments to permit work to be performed in difficult-to-reach areas, such as may occur during abdominal surgery. Some previously-used mechanisms include push-pull cables in guide tubes, pulley-cable mechanisms, and hydraulic mechanisms, however, these mechanisms are typically limited to one of axial or rotary movements and do not provide effective and precise use. For example, flexible push-pull cables have high drag and bending forces; cable-pulley mechanisms are complex and feeble; and hydraulic mechanisms typically are bulky and limited by hose travel.

In another example, there is also a need for mechanisms and features for hydraulically driven mechanisms that, among other things, allow motion and mechanical force transmission around bends to occur without the necessity of delivering hydraulic fluid around such bends, particularly where multiple hydraulic lines may be required (e.g., to produce rotation and grasping operationally downstream of a bend in a hydraulic arm or other extension).

Therefore, improvements in flexible wrist-type elements are desired.

SUMMARY OF THE INVENTION

The described aspects relate to flexible wrist-type elements capable of transmitting axial and/or rotational force around corners and bends. While the discussion of the aspects of the present invention that follows uses a remote surgical actuator for an illustrative purpose, it should be appreciated that the environment of the present invention is not limited to surgery and that the described aspects may be used in a variety of other environments. In particular, variations of the invention described herein can be used in any suitable actuating device or application. For example, aspects of the present invention may be used in manufacturing, construction, assembly lines, handling and disposing of hazardous materials, underwater manipulations, handling high temperature materials, or any other environment where a user may be remote from the item being manipulated or may experience fatigue when operating a mechanical device.

In one aspect of the present invention, a flexible wrist-type element, comprises: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position, wherein a point of intersection between the second longitudinal axis and the first longitudinal axis moves during movement between the first position and the second position; a driver assembly moveably supported by the base housing and the operational housing; and wherein the driver assembly is configured to actuate the operational element relative to the operational housing.

In another aspect of the present invention, a flexible wrist-type element, comprises: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position; a driver assembly moveably supported by the base housing and the operational housing; wherein the driver assembly is configured to actuate the operational element relative to the operational housing; and a first point on the operational housing configured such that, when an angle between the first longitudinal axis and the second longitudinal axis is varied, the first point on the operational housing traces a first curve; a second point on the operational housing configured such that, when the angle between the first longitudinal axis and the second longitudinal axis is varied, the second point on the operational housing traces a second curve, and wherein the first and second curves differ.

In another aspect of the present invention, a flexible wrist-type element, comprises: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position; a driver assembly moveably supported by the base housing and the operational housing; wherein the driver assembly is configured to actuate the operational element relative to the operational housing; and wherein the operational end pivots with respect to the base end via multiple pivot points.

In another aspect of the present invention, a flexible wrist-type element, comprises: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position; a driver assembly moveably supported by the base housing and the operational housing; wherein the driver assembly is configured to actuate the operational element relative to the operational housing; and wherein the driver assembly defines a path length between the base end and the operational end and the path length remains constant as an angle between the first longitudinal axis and the second longitudinal axis is varied.

In another aspect of the present invention, a flexible wrist-type element, comprises: a base housing extending along a first longitudinal axis towards a base end; an operational housing extending along a second longitudinal axis towards an operational end; an operational element moveably connected to the operational housing; a joint assembly movably connecting the base housing and the operational housing; wherein the joint assembly allows relative movement of the operational housing and the base housing between a first position and a second position; a driver assembly moveably supported by the base housing and the operational housing; wherein the driver assembly is configured to actuate the operational element relative to the operational housing when an angle between the first longitudinal axis and the second longitudinal axis assumes a value; an input element; and wherein the input element, the joint assembly and the operating end housing are connected via a three bar linkage.

Aspects of the present invention provide benefits and advantages that include the ability to transmit, direct and control actuation and motion around corners and bends. Aspects of the present invention may be used in remotely actuated systems, such as hydraulically actuated systems. Aspects of the present invention also provide benefits and advantages that include increased maneuverability and control. Thus, remotely actuated systems can be made more precise when actuated around corners and bends.

Additional advantages and novel features relating to the present invention will be set forth in part in the description that follows, and in part will become more apparent to those skilled in the art upon examination of the following or upon learning by practice of aspects of the invention.

BRIEF DESCRIPTION OF THE DRAWINGS

The present invention will become fully understood from the detailed description given herein below and the accompanying drawings, which are given by way of illustration and example only and thus not limited with respect to aspects of the present invention, wherein.

DETAILED DESCRIPTION OF ASPECTS OF THE PRESENT INVENTION

Aspects of the present invention will now be described more fully hereinafter with reference to the accompanying drawings, in which variations and aspects of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Overview of Components of the Present Invention

Figure 1:
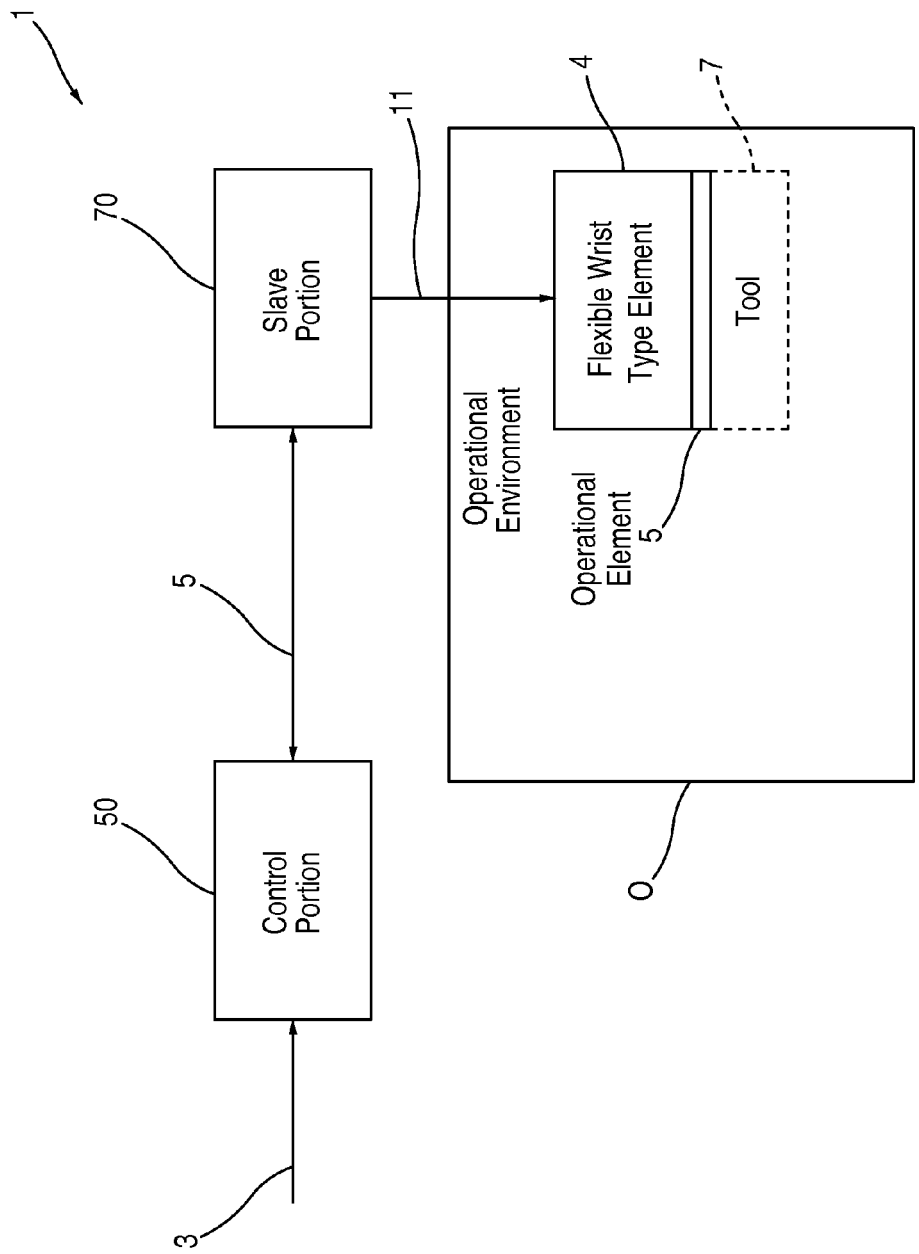
FIG. 1 is a schematic diagram of an exemplary system using a flexible wrist-type element in accordance with aspects of the invention.

FIG. 1 is a schematic diagram of an exemplary system 1 using a exemplary flexible wrist-type element 4 in accordance with aspects of the invention.

The system 1 may include a control portion 50 operable to receive an input 3, such as a force or motion, to drive the exemplary flexible wrist-type element 4 and/or tool 7, which may be connected to the exemplary flexible wrist-type element 4 via an operational element 5. The wrist element 4, operational element 5 and tool 7 form a slave portion 70 of system 1. The exemplary flexible wrist-type element 4 is generally capable of a variety of rotating, bending and grasping/cutting motions, discussed herein, that allow a user to position the tool 7, via the operational element 5, as needed in an operating environment O. Moreover, the exemplary flexible wrist-type element 4 generally has the flexibility of motion and maneuverability to allow the user to perform operations of varying complexity using the exemplary flexible wrist-type element 4, operational element 5 and tool 7 of system 1.

The input 3 is transferred from the control portion 50 to the slave portion 70 via a transfer mechanism 5, such as but not limited to a hydraulic system. System 1 may be configured to provide a given correlation between input 3 and the resultant output 11 that operates exemplary flexible wrist-type element 4 and/or tool 7 within the operational environment O. For example, input 3 may be a linear and/or rotational movement, and output 11 may be a linear and/or rotational movement, and such movements may be correlated in any fashion. For instance, a linear input 3 may be correlated to an output 11 that is linear or rotational, and a rotational input 3 may be correlated to an output 11 that is rotational or linear. Also, the relative degree of transfer may be controlled, e.g. such that a given amount of input 3 produces a given amount of output 11. Further, transfer mechanism 5 may additionally transfer feedback from exemplary flexible wrist-type element 4 and/or tool 7 back to control portion 50, thereby providing a user with a direct, tactile feel for the work being performed by the exemplary flexible wrist-type element 4 and/or tool 7. Also the transfer mechanism itself may be flexible and able to operate a remote slave system. In some cases the control portion and transfer mechanism may be a telemanipulation system. In one example of a suitable application for system 1, the exemplary flexible wrist-type element 4 and/or tool 7 may include an articulating device for performing surgery within a portion of a body of a patient. Thus, system 1 provides components to control, in a precise manner, actions of an exemplary flexible wrist-type element 4 and/or tool 7 in an operational environment O from a remote location.

Variations of aspects of the invention implemented in devices and systems, such as system 1 as well as others, may include a variety of possible movements and motions in both the control and slave portions. Herein, the ability to produce such motions in a system will be described as a "degree of freedom" or "providing a degree of freedom." The term "degree of freedom" is not meant to be used in a strict mathematical or physical sense. Rather, a "degree of freedom" is meant to refer to a certain motion or category of motions that are allowed in the control, slave or other portions of the system. The degrees of freedom of such a system are discussed in more detail in U.S. Provisional Patent Appl. No. 61/237,042, hereby incorporated by reference. For example, the system may include "macro" degrees of freedom that correspond to translations of an entire slave portion (e.g., rotate, forward/backward, etc.). The system may also include "micro" degrees of freedom that correspond to actuating some of the tools of the slave portion (e.g., grasping motion, etc.).

Figure 2:
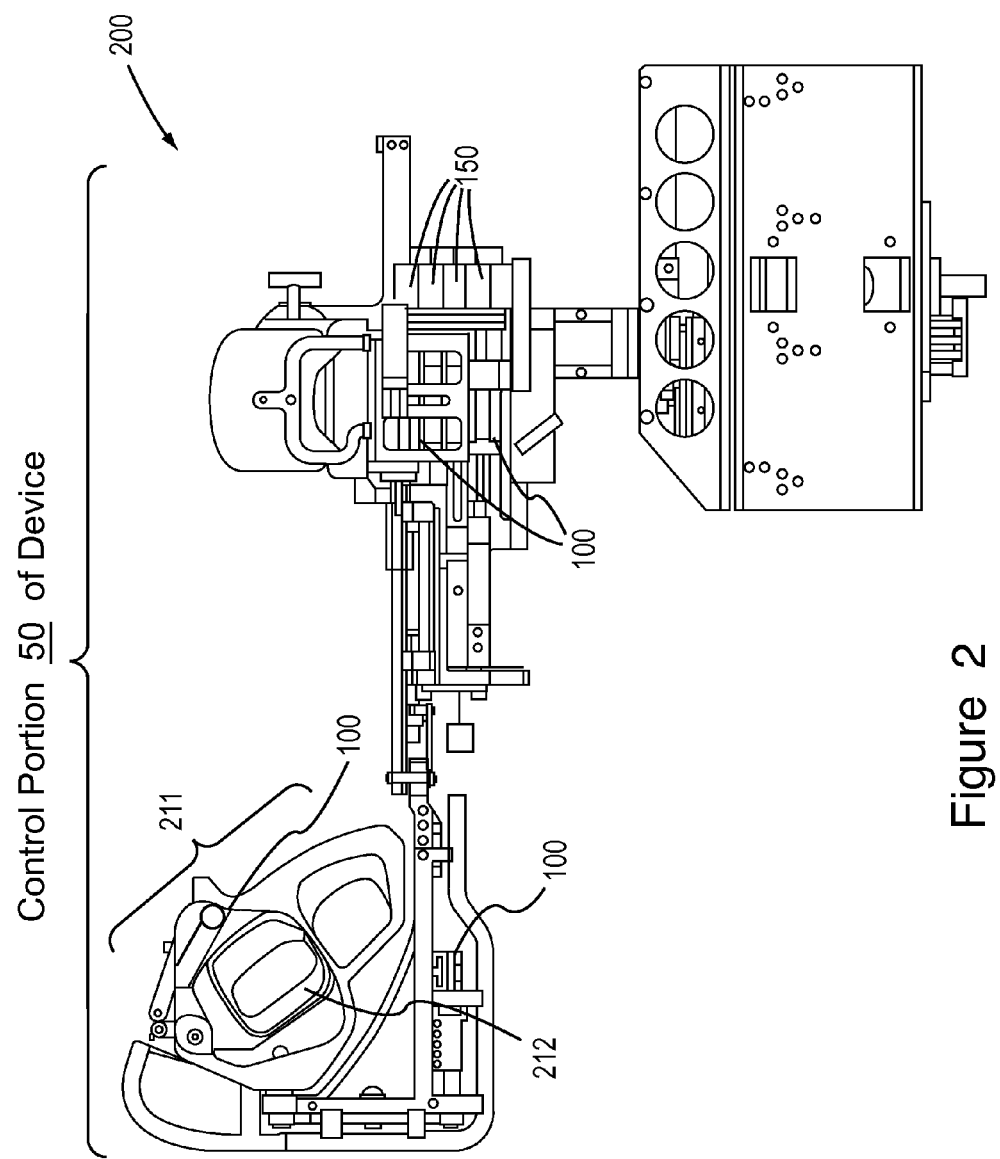
FIG. 2 is a side view of a variation of an exemplary control unit that may be used in conjunction with the present invention.

FIG. 2 is a detailed drawing of another variation of an exemplary control unit 200 that may be used in conjunction with the control portion 50 (FIG. 1). FIG. 2 shows several exemplary features of the control unit 200, including a handle 211, and a trigger loop 212 for interacting with the user. In some aspects of control unit 200, each degree of freedom corresponds to a corresponding control cylinder (or other control element) 100, and thus control unit 200 may include a plurality of control cylinders. Generally, to operate control unit 200, the user may grasp the handle 211, place one or more fingers inside the trigger loop 212 and squeeze the trigger loop 212 as well as move the handle 211 in various directions. This motion and similar motions generally produce a mechanical response in one or more respective control cylinders 100, which transmit the mechanical response to the corresponding one or more slave actuators 22 in the slave portion 70 of the system 1.

Figure 3:
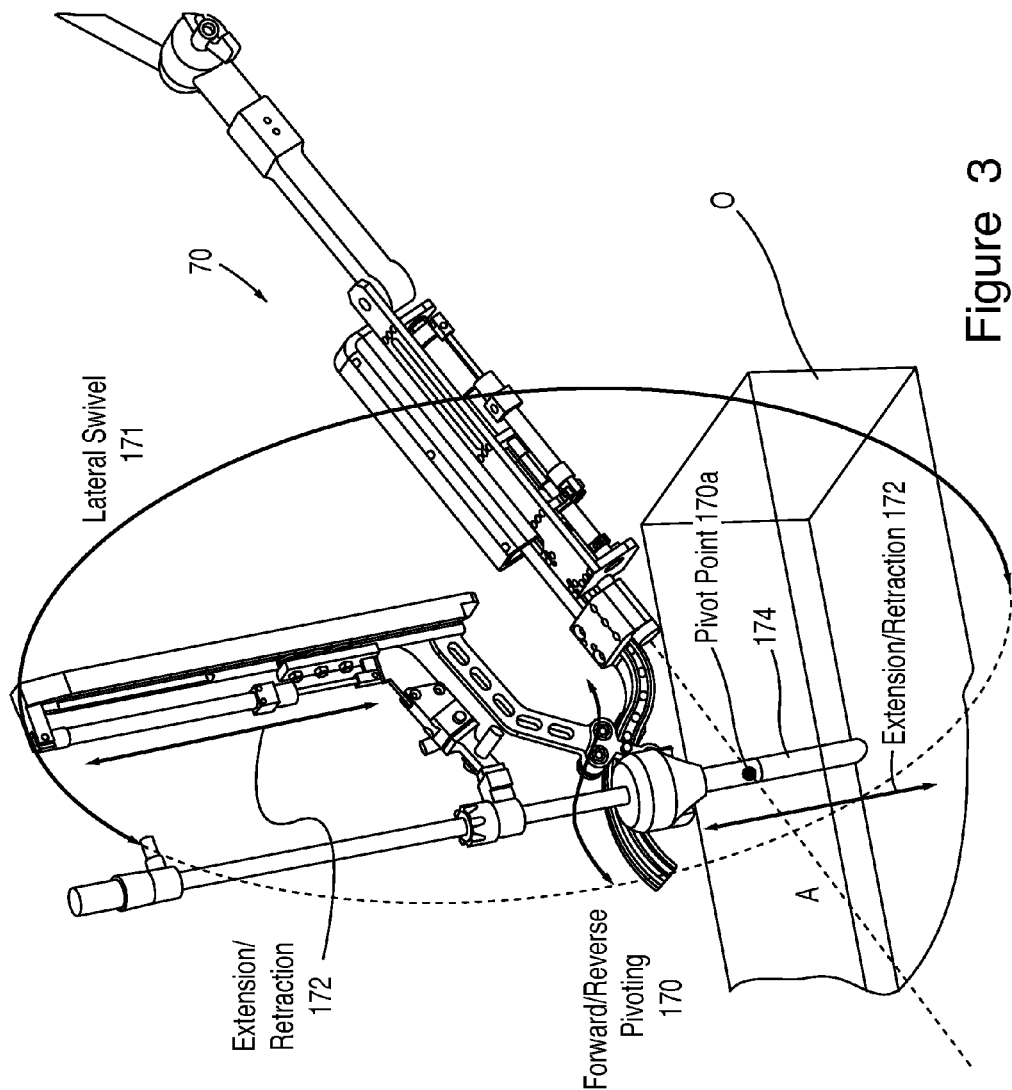
FIG. 3 is a side view of an exemplary slave portion that may be used in conjunction with the present invention.

FIG. 3 is a side view of an exemplary slave portion 70 that may be used in conjunction with the present invention. FIG. 3, in particular, gives an overview of three exemplary macro degrees of freedom in a variation of the slave portion of the device in accordance with aspects of the present invention. This figure and discussion are meant to introduce three exemplary degrees of freedom that are discussed in more detail with their associated controlling and actuating mechanisms in U.S. Provisional Patent Appl. No. 61/237,042. It should be noted that, while the exemplary degrees of freedom are useful for certain applications, they are not meant to be exhaustive. Other degrees of freedom are within the scope of the invention. Indeed, it is possible to modify the existing apparatus as described to encompass either additional or fewer degrees of freedom, as needed. All such modifications should be considered within the scope of the present invention.

In FIG. 3, one of the exemplary macro degree of freedom shown is Forward/Reverse Pivoting 170 of the exemplary flexible wrist-type element 4 and related components. Forward/Reverse Pivoting 170 may allow exemplary flexible wrist-type element 4 to pivot about a central pivot point, such as Pivot Point 170a shown in FIG. 3. This particular degree of freedom is useful for, among other things, positioning the exemplary flexible wrist-type element 4 about a particular area of interest in an operational environment O. For example, the Forward/Reverse Pivoting 170 degree of freedom can be used to position a tool, such as a scalpel, on the end of the exemplary flexible wrist-type element 4 in a position appropriate for the making of an incision. Alternatively, Forward/Reverse Pivoting 170 degree of freedom can be used to position tweezers on the end of the exemplary flexible wrist-type element 4 in a position appropriate for grasping a particular object (e.g., an organ or tissue).

In FIG. 3, another of the exemplary macro degree of freedom shown is Lateral Swivel 171 of the exemplary flexible wrist-type element 4 and related components. The Lateral Swivel 171 may allow exemplary flexible wrist-type element 4 to swivel about axis A. This particular degree of freedom is useful for, among other things, positioning the exemplary flexible wrist-type element 4 about a particular area of interest in an operational environment O. The Lateral Swivel 171 degree of freedom can be used, for example, to position a scalpel on the end of the exemplary flexible wrist-type element 4 in a position appropriate for the making of an incision. Alternatively, Forward/Reverse Pivoting 170 degree of freedom can be used to position tweezers on the end of the exemplary flexible wrist-type element 4, via the operational element 5, in a position appropriate for grasping a particular object (e.g., an organ or tissue).

In FIG. 3, another of the exemplary macro degree of freedom shown is Extension/Retraction 172 of the exemplary flexible wrist-type element 4 and related components. Extension/Retraction 172 may allow exemplary flexible wrist-type element 4 to be brought closer to or further away from a certain position within the operational environment O. This particular degree of freedom may, for example, allow the exemplary flexible wrist-type element 4 to be retracted a safe distance from objects in the operating environment while it is repositioned using the Forward/Reverse Pivoting 170 and Lateral Swivel 171 motions. Once the operational element 5 has been repositioned, it may be brought back in contact or in close proximity with the operational environment O, or objects therein, using the Extension/Retraction 172 degree of freedom.

Figure 4A:
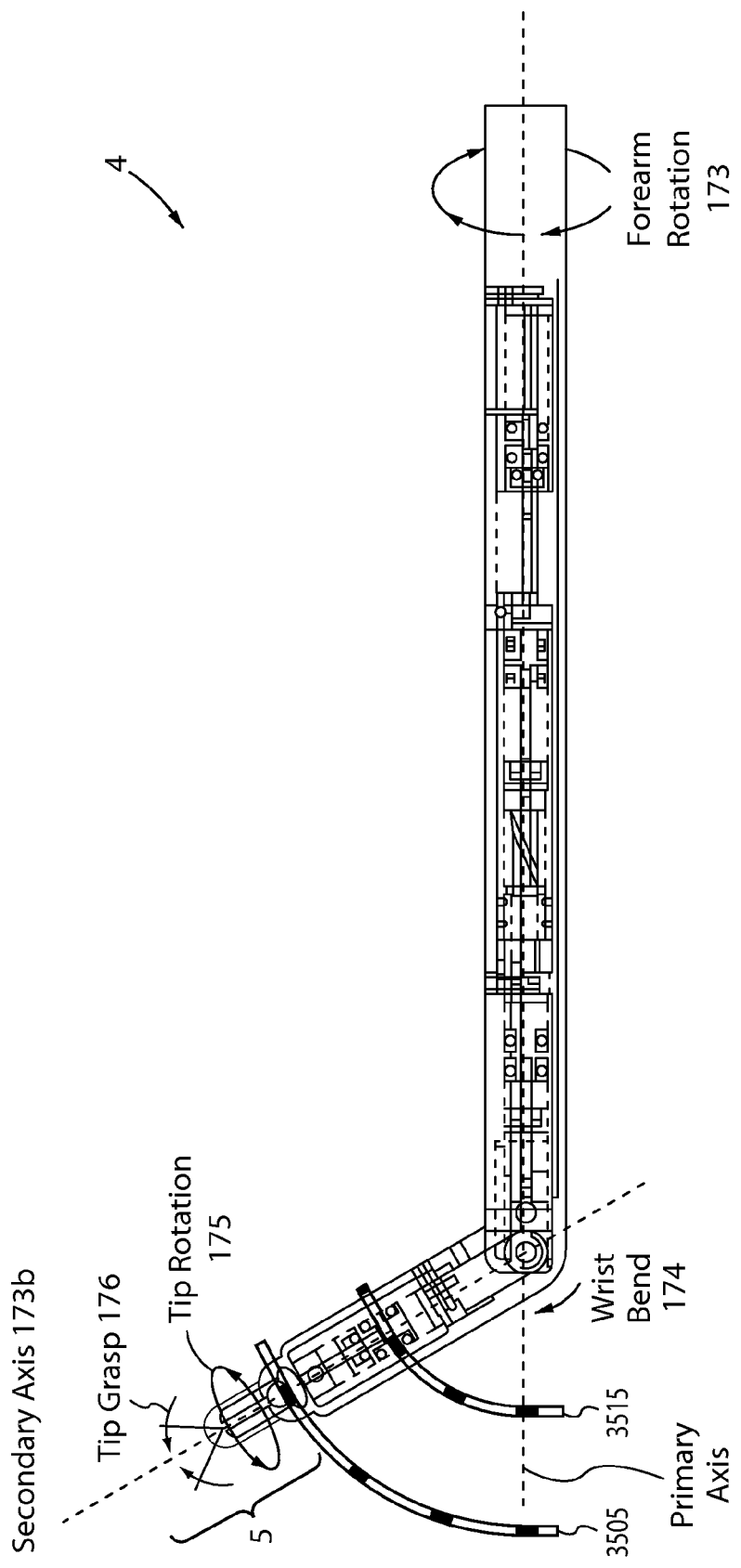
FIG. 4A is a close-up side view of an end of an exemplary operational element 5 that may be used in conjunction with the present invention.

FIG. 4A is a close-up side view of an end of an exemplary flexible wrist-type element 4, including operational element 5, that may be used in conjunction with the present invention. Note that FIG. 4A does not show a tool 7 attached to the end of operational element 5. It is to be understood that various motions described with respect to the operational element 5 will also apply to any tool 7 attached to the operational element 5.

FIG. 4A also shows an overview of four exemplary micro degrees of freedom in an instrument and/or tool in accordance with aspects of the present invention. The four exemplary degrees of freedom are discussed in more detail below in U.S. Provisional Patent Appl. No. 61/237,042. It should be noted that, while the exemplary degrees of freedom are useful for certain applications, they are not meant to be exhaustive. Other degrees of freedom are within the scope of the invention. Indeed, it is possible to modify the existing apparatus as described to encompass either additional or fewer degrees of freedom, as needed. All such modifications should be considered within the scope of the present invention.

In FIG. 4A, one of the exemplary micro degrees of freedom shown is the Forearm Rotation 173 of the wrist element 4 and related components. Forearm Rotation 173 may allow wrist element 4 and operational element 5 be actuated, such as by rotating about a primary axis 173*a* of the wrist element 4. This particular degree of freedom is useful for, among other things, positioning the wrist element 4 about a particular area of interest in an operational environment O. For example, the Forearm Rotation 173 degree of freedom can be used to position a tool, such as scalpel, fixed to the operational element 5 of the wrist element 4 in a position appropriate for the making of an incision. Additionally, for example, the Forearm Rotation 173 degree of freedom can be used to sweep a cutting motion with the scalpel on the end of the wrist element 4. In another example, the Forearm Rotation 173 degree of freedom can be used to position a tool, such as tweezers, on the end of the wrist element 4 in a position appropriate for grasping a particular object (e.g., an organ or tissue).

Also in FIG. 4A, another one of the exemplary micro degrees of freedom shown is the Wrist Bend 174 of the wrist element 4 and related components. Wrist Bend 174 may allow operational element 5 to bend with respect to the primary axis 173*a* of the wrist element 4. This particular degree of freedom is useful for, among other things, positioning a portion of the operational element 5 and/or a tool about a particular area of interest in an operational environment O. For example, the Wrist Bend 174 degree of freedom can be used to position a scalpel on the end of the wrist element 4 in a position appropriate for the making of an incision. For instance, the Wrist Bend 174 degree of freedom can be used to sweep a cutting motion with scalpel on the end of the operational element 5. In another example, the Wrist Bend 174 degree of freedom can be used to position tweezers on the end of the operational element 5 in a position appropriate for grasping a particular object (e.g., an organ or tissue).

Further, in FIG. 4A, two additional exemplary micro degrees of freedom shown are Tip Rotation 175 and Tip Grasp 176 of the tip or operational element 5 and related components. Tip Rotation 175 may allow operational element 5 and/or tool to be actuated, such by rotating about primary axis 173*a*, or to rotate about a secondary axis 173*b* formed after bending a portion of wrist element 4 relative to primary axis 173*a*. Tip Grasp 176 may allow operational element 5 and/or tool to bend with respect to the primary axis 173*a* of the wrist element 4, or to bend about a secondary axis 173*b* formed after bending a portion of wrist element 4 relative to primary axis 173*a*. Further, for example, Tip Grasp 176 may allow a relative bending or pivoting of two corresponding instrument or tool portions, e.g. pincher arms, to grasp or release an item. These particular degrees of freedom are useful for, among other things, positioning the operational element 5 and/or tool about a particular area of interest in an operational environment O. For example, the Tip Rotation 175 and Tip Grasp 176 degrees of freedom can be used to position a scalpel on the end of the operational element 5 in a position appropriate for the making of an incision. Additionally, for example, the Tip Rotation 175 and Tip Grasp 176 degrees of freedom can be used to sweep a cutting motion with scalpel on the end of the operational element 5. In another example, the Tip Rotation 175 and Tip Grasp 176 degrees of freedom can be used to position tweezers on the end of the operational element 5 in a position appropriate for grasping or releasing a particular object (e.g., an organ or tissue).

Overview of Aspects of the Invention

Figure 4B:
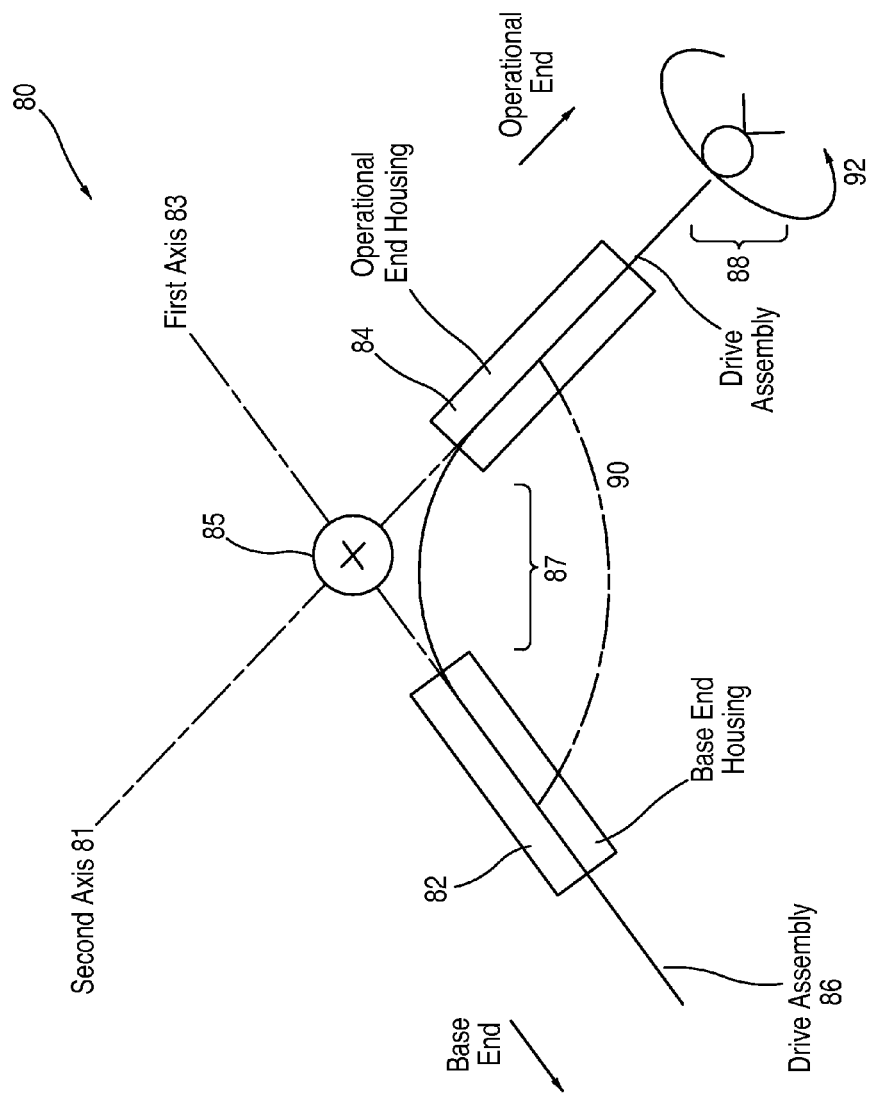
FIG. 4B is a schematic illustrating mechanical rotate-after-bend that may be accomplished during the Wrist Bend 174 motion shown in FIG. 4A.

FIG. 4B is a schematic illustrating a rotate-after-bend motion that may be accomplished by an exemplary flexible wrist-type element 80 during the Wrist Bend 174 motion shown in FIG. 4A. It is to be understood that the exemplary flexible wrist-type element 80 pertains to aspects of each of the variations of the invention discussed herein, including the exemplary flexible wrist-type element 4 of FIG. 4A.

Exemplary flexible wrist-type element 80 includes several components, including: a base housing 82 extending along a first longitudinal axis 83, an operational housing 84 extending along a second longitudinal axis 81, an intersection point 85 where the first 83 and second 81 longitudinal axes meet, an operational element 88 and a drive assembly 86 that allows actuation of the operational element 88 from the base end of the exemplary flexible wrist-type element 80.

Generally, the base end housing 82 and the operational end housing 84 are connected by a joint assembly 87 that allows relative motion of the base end housing 82 and the operational end housing 84.

As shown in FIG. 4B, the exemplary flexible wrist-type element 80 may bend such that the first 83 and second 81 longitudinal axes meet make an angle 90 with respect to one another. Regardless of the bend angle 90, however, the drive assembly 86 is configured such that it is able to actuate certain motions in the operational element 88. For example, FIG. 4B shows that the drive assembly 86 is able to actuate a rotational motion 92 of the operational element 88 about the second axis 81 regardless of the value of the angle 90. In some variations of the present invention, this actuation of the rotational motion 92 of the operational element 88 is performed by the drive assembly 86 in a purely mechanical manner, e.g., without the substantial use of signals transferred by electrical, optical or other devices. The drive assembly may also be capable of axial motion, along direction 86a shown in FIG. 4B, and capable of imparting that axial motion to the operational element.

Figure 4C:
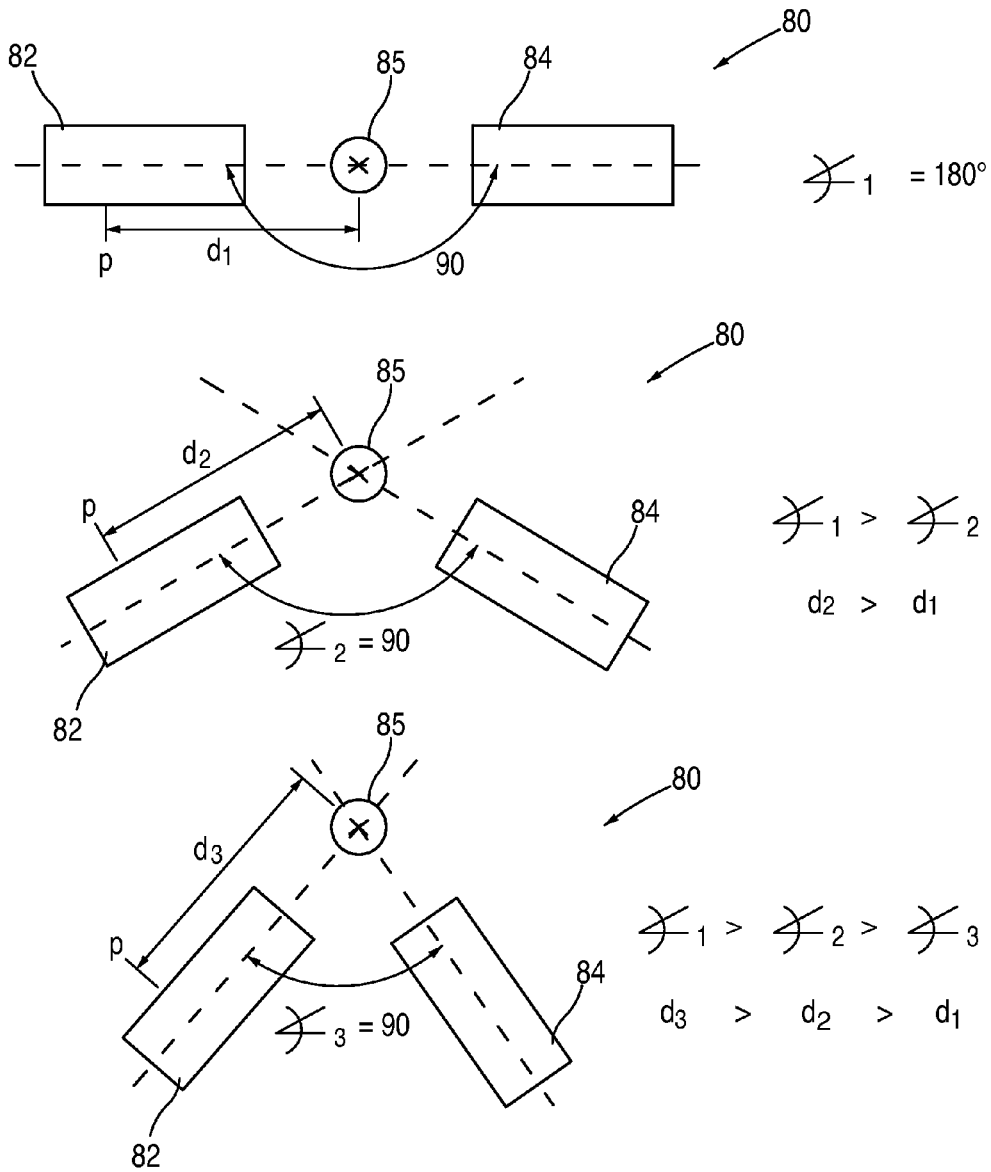
FIG. 4C is a schematic illustrating relative motion of the intersection point of the exemplary flexible wrist-type element of FIG. 4B during bending.

FIG. 4C is a schematic illustrating relative motion of the intersection point of the exemplary flexible wrist-type element of FIG. 4B during the Wrist Bend 174 motion shown in FIGS. 4A and 4B. For clarity, only the base end housing 82, operational end housing 84, first 83 and second 81 longitudinal axes and their intersection point 85 are shown. In portion (1) of FIG. 4C, the relative angle 90 between the first 83 and second 81 longitudinal axes is about 180° (angle 1). In this configuration, the distance between an arbitrary point P on the base end housing 82 and the intersection point 85 is d1. As shown in portion (2) of FIG. 4C, the exemplary flexible wrist-type element 80 can be bent such that the relative angle 90 takes on a value less than 180° (angle 2). In this case, the intersection point 85 may move with respect to the point P on the base housing 82 such that the distance between P and the intersection point 85 is now d2, which is greater than d1. This distinguishes the exemplary flexible wrist-type element 80 from a conventional hinge where the distance between a pivot point and any other point on the hinge remains fixed. As shown in portion (3) of FIG. 4C, the exemplary flexible wrist-type element 80 can be bent such that the relative angle 90 takes on a value less than angle 2 (e.g., angle 3). In this case, the intersection point 85 moves further still with respect to the point P on the base housing 82 such that the distance between P and the intersection point 85 is now d3, which is greater than d2.

Figure 4D:
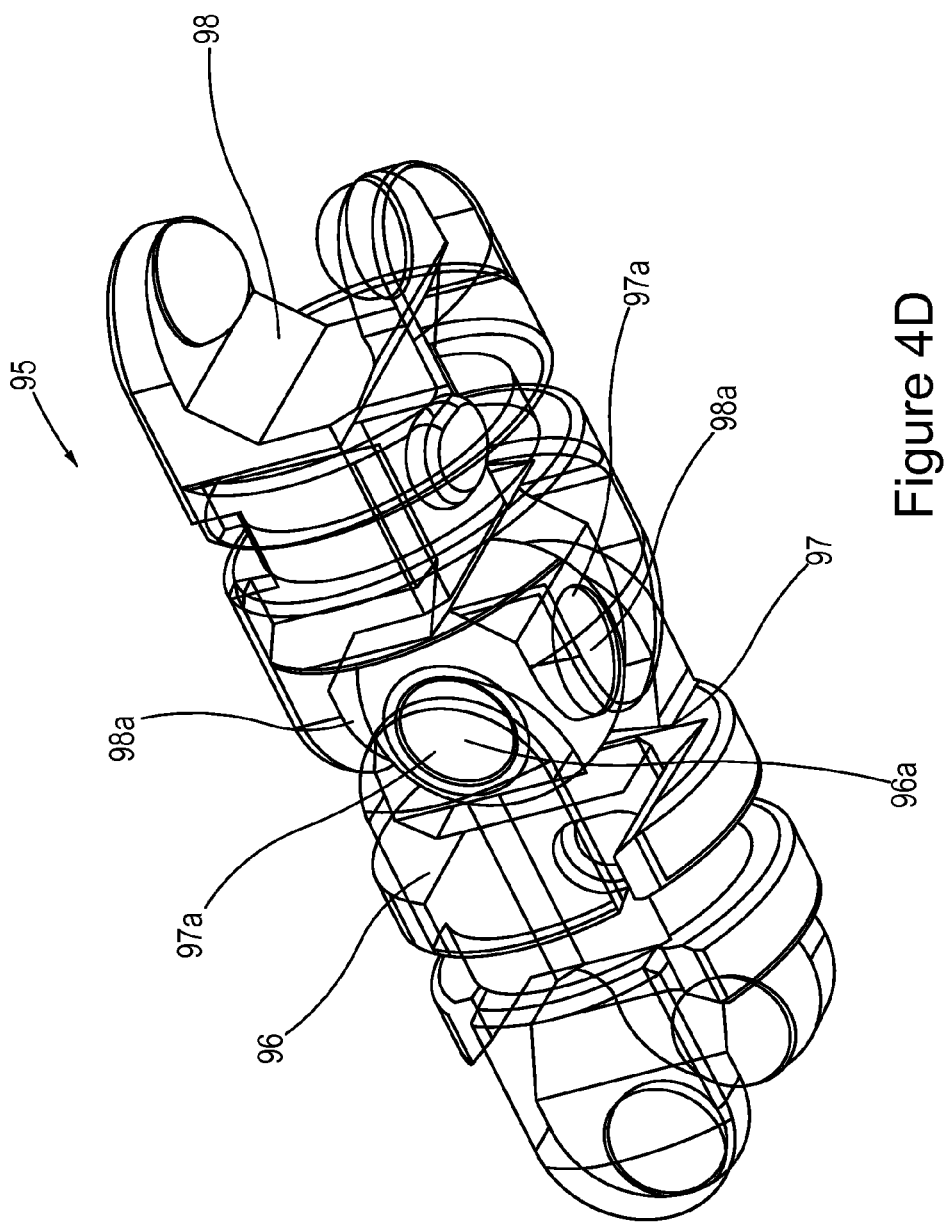
FIG. 4D is a partially transparent view of an flexible drive assembly that can be used in conjunction with variations of the present invention.

FIG. 4D is a partially transparent view of an flexible drive assembly that can be used in conjunction with variations of the present invention, for example, as a portion of drive assembly 86. The flexible drive assembly 95, for example, may be used to transmit motion from the base end to the operational end of drive assembly 86 as the exemplary flexible wrist-type element 80 undergoes the bending motion shown in FIG. 4C. Each U-joint portion 96 and 98 is fixed about a pivoting element 97. Pivoting element 97 may, for example, be a solid ball with depressed features 97a for mating with aspects 98a of the U-joint portion 98 or aspects 96a of U-joint portion 96, for example. Note that each U-joint portion 96 and 98 is partially transparent to show the mating of depressed features 97a with aspects 96a and 98a. Other variations of the U-joint 95 are also possible. For example, U-joint 95 may include other variations of the pivoting element 97 that may, for example, be hollow and/or have more complicated depressed features 97a. U-joint portion 96 and 98 may have any suitable shape to interface with the pivoting element 97. Additionally or alternatively, any suitable variation of Hooke's or universal joints may be used, including constant velocity joints. Additionally or alternatively other flexible elements such as cables, hoses, wires, flexible rods, may be used.

First Four Bar Flexible Wrist-Type Element

Figure 5:
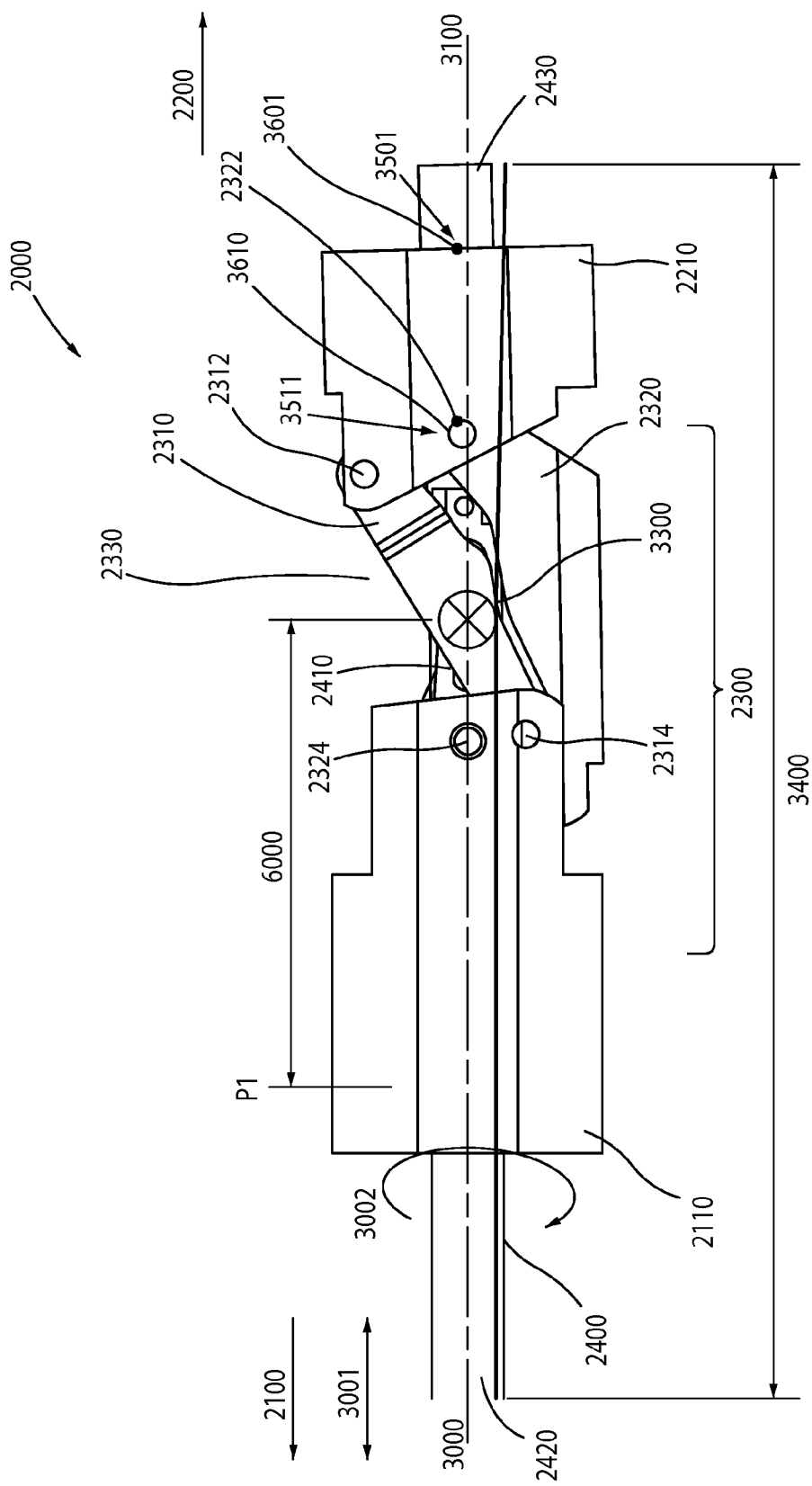
FIG. 5 is a side view of an end of an exemplary flexible wrist-type element that may be used in conjunction with the present invention in non-bending position.
Figure 6A:
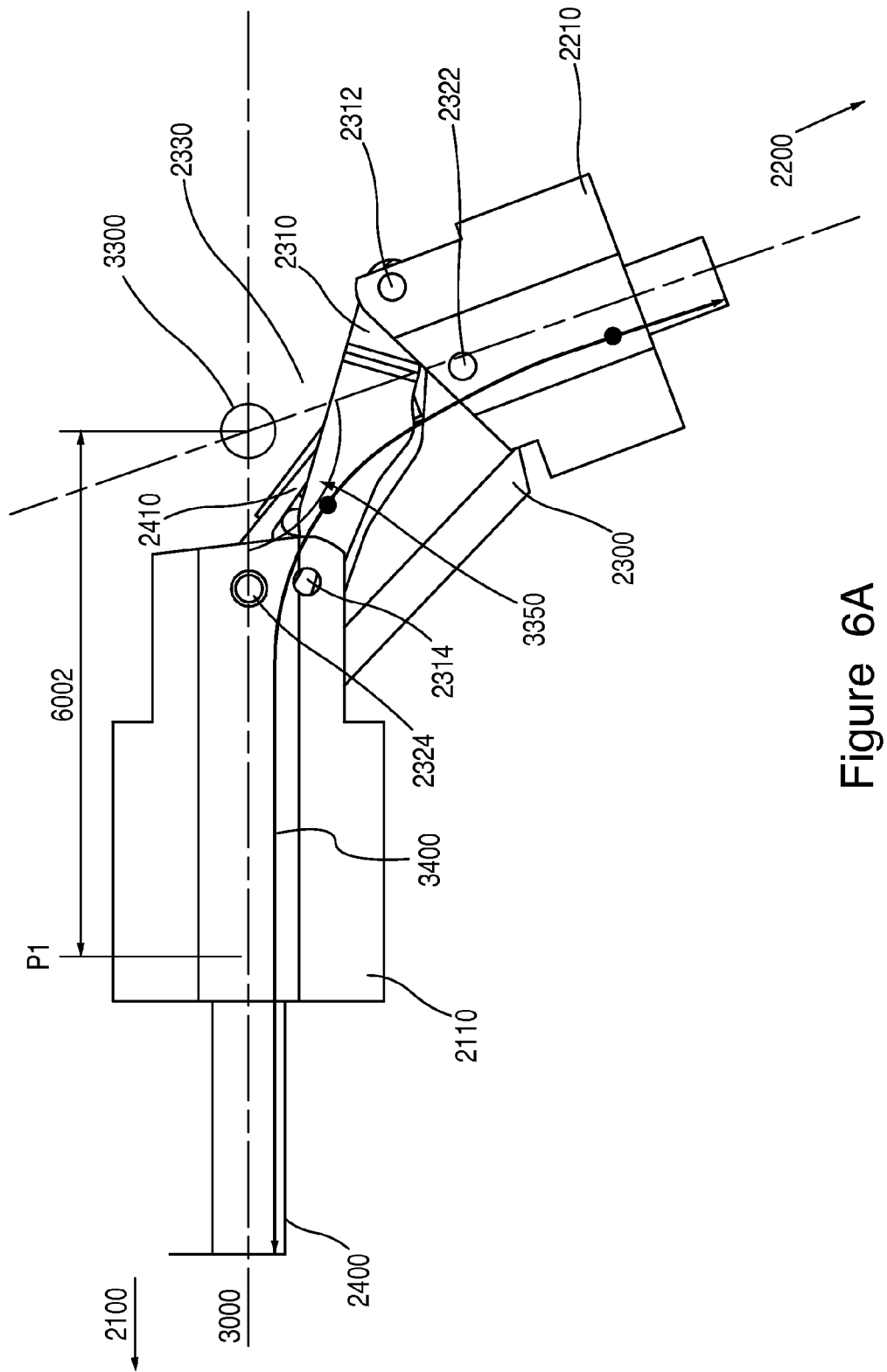
FIG. 6A is a side view of an end of the exemplary flexible wrist-type element of FIG. 5 in a first bending position.
Figure 7:
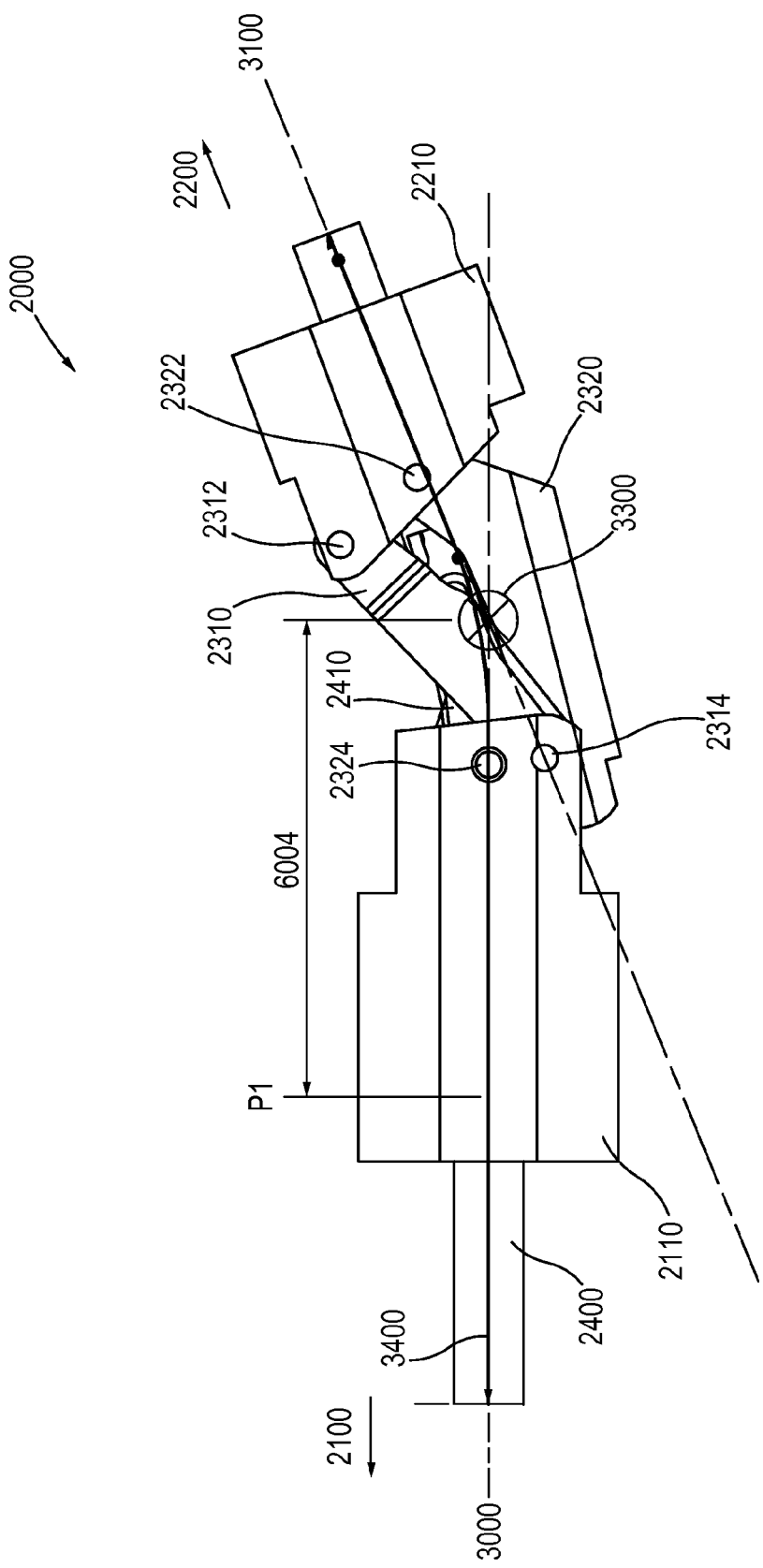
FIG. 7 is a side view of an end of the exemplary flexible wrist-type element of FIG. 5 in a second bending position.
Figure 8:
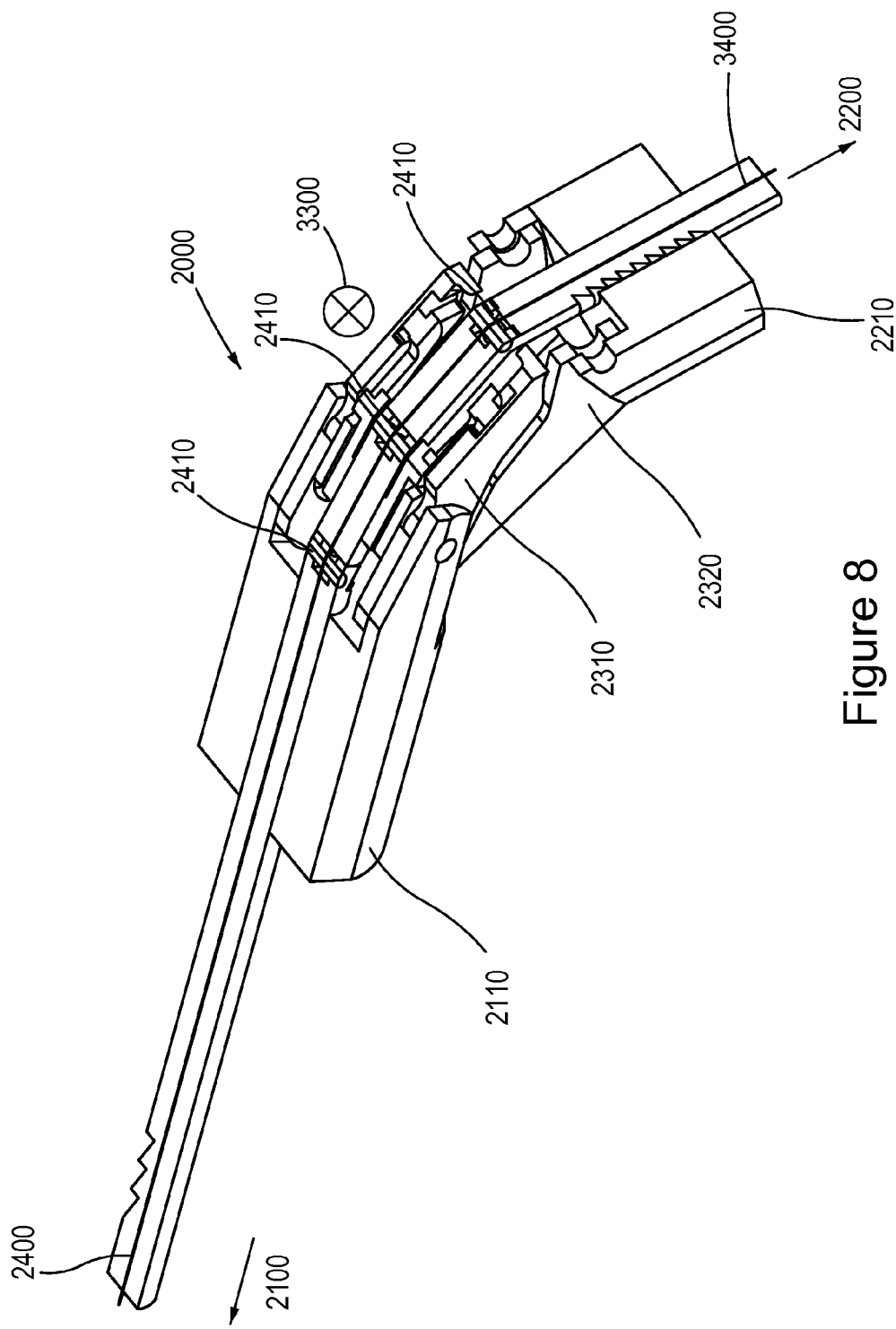
FIG. 8 is a cross-sectional view of the exemplary flexible wrist-type element of FIGS. 5-7 when it is bent.

FIG. 5 is a side view of an end of an exemplary flexible wrist-type element that may be used in conjunction with the present invention in non-bending position. FIGS. 6 and 7 are side views of the base end 2100 and operational end 2200 illustrating relative motion during the course of operation. Such relative movement, as shown in FIGS. 6 and 7, may, for example, correspond to the Wrist Bend 174 motion shown in FIG. 4A. FIG. 8 shows a cross-sectional view of the exemplary flexible wrist-type element of FIGS. 5-7 when it is bent.

As shown in FIG. 5, the exemplary flexible wrist-type element 2000 includes a base end 2100 and an operational end 2200 separated by joint assembly 2300. Generally the, base end 2100 includes a base housing 2110 and the operational end 2200 includes an operational end housing 2210. The base housing 2110 and the operational end housing 2210 may be of any suitable shape, including the shapes illustrated in FIG. 5. The base housing 2110 and the operational end housing 2210 may be monolithic, as shown in FIG. 5, or may contain any suitable number of subsidiary pieces, components and/or fixtures. A driver assembly 2400 extends from the base end 2100 to the operational end 2200 and generally allows remote actuation of an operational element, such as operational element 5 shown in FIG. 4A, at the operational end 2200 even when the axis meeting angle 3350 is nonzero. The driver assembly 2400 is generally flexible and capable of bending, twisting, pivoting and/or rotating motions.

More particularly, the base end 2100 of the exemplary flexible wrist-type element 2000 defines a first axis 3000 and the operational end 2200 defines a second axis 3100 that meet at an intersection point 3300. The intersection point 3300 may or may not be located on the joint assembly 2300. When the base end 2100 and operational end 2200 move relative to each other, as shown in FIGS. 5-7, the intersection point 3300 may move relative to one, or both, of the operational end 2200 and the base end 2100. For example, in FIG. 5, the intersection point 3300 and point P1 on the base end 2100 are spaced apart by a distance 6000. When the base end 2100 and operational end 2200 are moved relative to one another in a bending motion, as shown in FIG. 6A, the distance between the intersection point 3300 and point P1 on the base end 2100 is increased to distance 6002, which is greater than distance 6000. On the other hand, when the base end 2100 and operational end 2200 are moved relative to one another in another bending motion, as shown in FIG. 7, the distance between the intersection point 3300 and point P1 on the base end 2100 is decreased to distance 6004, which is less than distance 6000. These relative motions of the intersection point 3300 and components of the exemplary flexible wrist-type element 2000 are meant to be purely exemplary. Any other suitable relative motion of the intersection point 3300 with respect to the components of the exemplary flexible wrist-type element 2000 are included in the present invention. For example, the intersection point 3300 may move in substantially the opposite manner as shown in FIGS. 5-7. Alternatively, the intersection point 3300 may remain fixed with respect to components of the exemplary flexible wrist-type element 2000, or undergo motion along a complex curve.

In some relative positions, the first axis 3000 and the second axis 3100 meet at the intersection point 3300 such that their intersection defines axis meeting angle 3350 (FIG. 6A). The joint assembly 2300 can be used to move the base housing 2110 relative to the operational end housing 2210 such that the axis meeting angle 3350 the first axis 3000 and the second axis 3100 sweeps through a range of values. For example, the axis meeting angle 3350 may range in value from ±135°. Alternatively, in some embodiments, the axis meeting angle 3350 may range in value from as much as or more than ±90°. Although FIG. 5 shows a joint assembly 2300 that is restricted in motion such that the maximum negative value of the axis meeting angle 3350 is smaller than the maximum positive value of the axis meeting angle 3350, this is not necessarily the case. It is to be understood that the joint assembly 2300 can be constructed such that the maximum values of the axis meeting angle 3350 in both positive directions are equal, or that either one exceeds the other. The relative magnitude of the maximum values of the axis meeting angle 3350, in general, should depend on the particular application.

As shown in FIG. 5, the joint assembly 2300 includes at least two pivotable sections, first pivotable section 2310 and second pivotable section 2320. The inclusion of the first pivotable section 2310, second pivotable section 2320, base end housing 2100 and the operational end housing 2210 are the four elements that define the "4 bar" linkage of the device. The first pivotable section 2310 and second pivotable section 2320 may be of any suitable shape, including the shapes illustrated in FIG. 5. The first pivotable section 2310 and second pivotable section 2320 may be monolithic, as shown in FIG. 5, or may contain any suitable number of subsidiary pieces, components and/or fixtures. The first pivotable section 2310 and second pivotable section 2320 may cooperate with the operational end housing 2210 and the base housing 2110 to move exemplary flexible wrist-type element 2000 through a range of motion. For example, the first pivotable section 2310 and second pivotable section 2320 may move relative to one another, for example, such as through the positions shown in FIGS. 5-7. In addition, the first pivotable section 2310 and second pivotable section 2320 may be configured to be capable of imparting other types of motion to the exemplary flexible wrist-type element 2000.

The first pivotable section 2310 may further be pivotably connected to the base end housing 2110 via a first base end pivot point 2314. In addition, as shown in FIG. 5, the joint assembly 2300 may further include a second pivotable section 2320. The second pivotable section 2320, as shown in FIG. 5, is pivotably connected to the operational end housing 2210 by a second operational end pivot point 2322. The second pivotable section 2320 may further be pivotably connected to the base end housing 2110 via a second base end pivot point 2324. As shown in FIG. 5, the second pivotable section may be disposed next to the first pivotable section 2310. Alternatively, the second pivotable section 2320 and the first pivotable section 2310 may have one of a number of suitable relationships, including: being placed side-by-side, placed such that one pivotable section is nested within the other or other suitable relationships. Although only two pivot points are shown for each of the first pivotable section 2310 and second pivotable section 2320 in FIG. 5, it is to be understood that the number of pivot points is not limited to that number. Any suitable number of pivot points is possible and additional pivot points may provide additional range of motion to the joint assembly 2300.

Sweeping the axis meeting angle 3350 is accomplished using the various components of the joint assembly 2300. For example, the joint assembly 2300 may include a first pivotable section 2310 pivotably connected to the operational end housing 2210 by a first operational end pivot point 2312. In general, there may be two first operational end pivot points 2312 on either side of the 2300 such that the profile shown in FIG. 5 shows one side of a symmetrical device. However, it is to be understood that there is no requirement for the device to be symmetrical and, in fact, it is possible for the device to operate with only a single first operational end pivot point 2312. Motion of the operational end housing 12210 relative to the base end housing 12110, as facilitated by the first pivotable section 2310 and the second pivotable section 2320. causes a relative movement of the first 13000 and second 13100 longitudinal axes sweeping through values of the axis meeting angle 13350 (e.g., as shown in FIG. 4C).

Generally, the driver assembly 2400 establishes a mechanical link between the base end 2100 and the operational end 2200. The driver assembly 2400 is best shown in FIG. 8. As discussed above, the operational end 2200 may include an operational element, such as, for example, the operational element 5 shown in FIG. 4A, that can be actuated by the driver assembly 2400. For example, control unit 200 (FIG. 2) may be coupled to the driver assembly 2400 via hydraulic actuators in the manner described in the context of FIG. 4A. In such a configuration, a user's motions while operating the control 2000 may be transferred, for example hydraulically, to the driver assembly 2400. The driver assembly 2400, then, may transfer the same motions (or amplified version of such motions) mechanically to the operational element 5. In this way the driver assembly 2400 may act as a mechanical conduit between the control assembly 200 and the operational element 5. Such a configuration may be used to perform each of the micro motions shown in FIG. 4A. For example, actuation of the control unit 200 may cause the driver assembly 2400 to cause the operational element 5 to perform one or more of the Tip Grasp 176, Tip Rotation 175, Wrist Bend 174 or Forearm Rotation 173 motions shown in FIG. 4A.

The driver assembly 2400 may, for example, be able to transfer mechanical motion to, actuate or mechanically communicate with the operational element 5 such that the operational element 5 can, for example, perform some or all of the micro motions shown in FIG. 4A. For example, the Tip Grasp 176 motion may be actuated by moving the driver assembly 2400 along direction 3001, a direction that is co-incident and co-linear with the path length 3400 made by the driver assembly 2400 throughout the exemplary flexible wrist-type element 2000. The Tip Rotation 175 motion, for example, may be actuated by rotating the driver assembly 2400 along rotational direction 3002 with respect to the base end housing 2110 and the operational end housing 2210.

The driver assembly 2400 may include, for example, one or more u-joints 2410, as shown in FIGS. 5 and 6 in order to, among other things, transfer mechanical motion to, actuate or mechanically communicate with the operational element 5. U-joints 2410 may, for example, be similar to the U-joint 95 shown in FIG. 4D. The u-joints 2410 may allow the driver assembly 2400 to maintain mechanical communication between a base end section 2420 and an operational end section 2430 of the driver assembly 2400 even as the exemplary flexible wrist-type element 2000 is bent, as shown, for example, in FIG. 6A. Maintaining mechanical communication in this way enables the driver assembly 2400 to actuate the operational element 5 in the manner described above even when the joint assembly 2300 is bent in a Wrist Bend 174 motion, as shown, for example, in FIG. 6A. The driver assembly 2400 could also or alternatively be fashioned from other flexible mechanical devices such as, for example, push-pull cables or other cables. This wrist structure, and any of the wrist structures discussed herein could be used to maintain even path length for non-driving elements, such as wires, hoses, etc.

Generally the joint assembly 2300 is constructed so that the path length 3400 remains substantially constant during a Wrist Bend 174 (FIG. 4A, FIGS. 5-7). Keeping the path length 3400 constant during such a bend maintains a given state of the operational element 5 regardless of the relative positions of the base end housing 2100 and the operational end housing 2210. In other words, if the path length of the driver assembly 2400 changes relative to the operational end, then a state of the Tip Grasp 176, or any other motion controlled by a push or pull movement of the driver assembly 2400, would change as the movement would cause an increase or decrease in a grasping state. The path length 3400 may be kept constant using a variety of configurations. As shown in FIGS. 5-7, one exemplary configuration that keeps the path length constant is to construct the first pivotable section 2310 and the second pivotable section 2320, as shown in FIG. 6A, when the exemplary flexible wrist-type element 2000 exercises a Wrist Bend 174 motion (as shown in FIG. 4A and FIGS. 5-7).

Figure 6B:
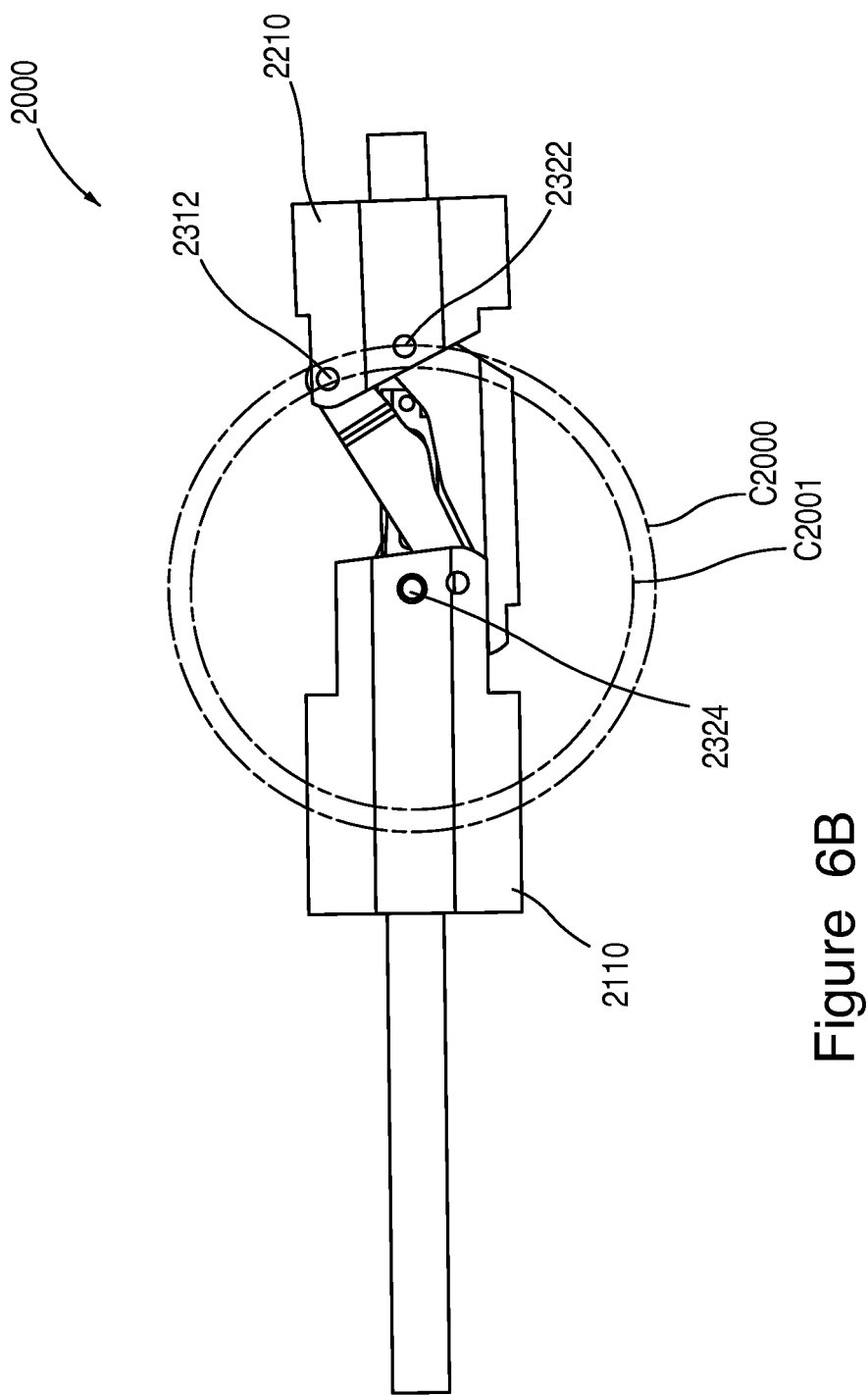
FIG. 6B is a side view of an end of the exemplary flexible wrist-type element of FIG. 5 in a first position.
Figure 6C:
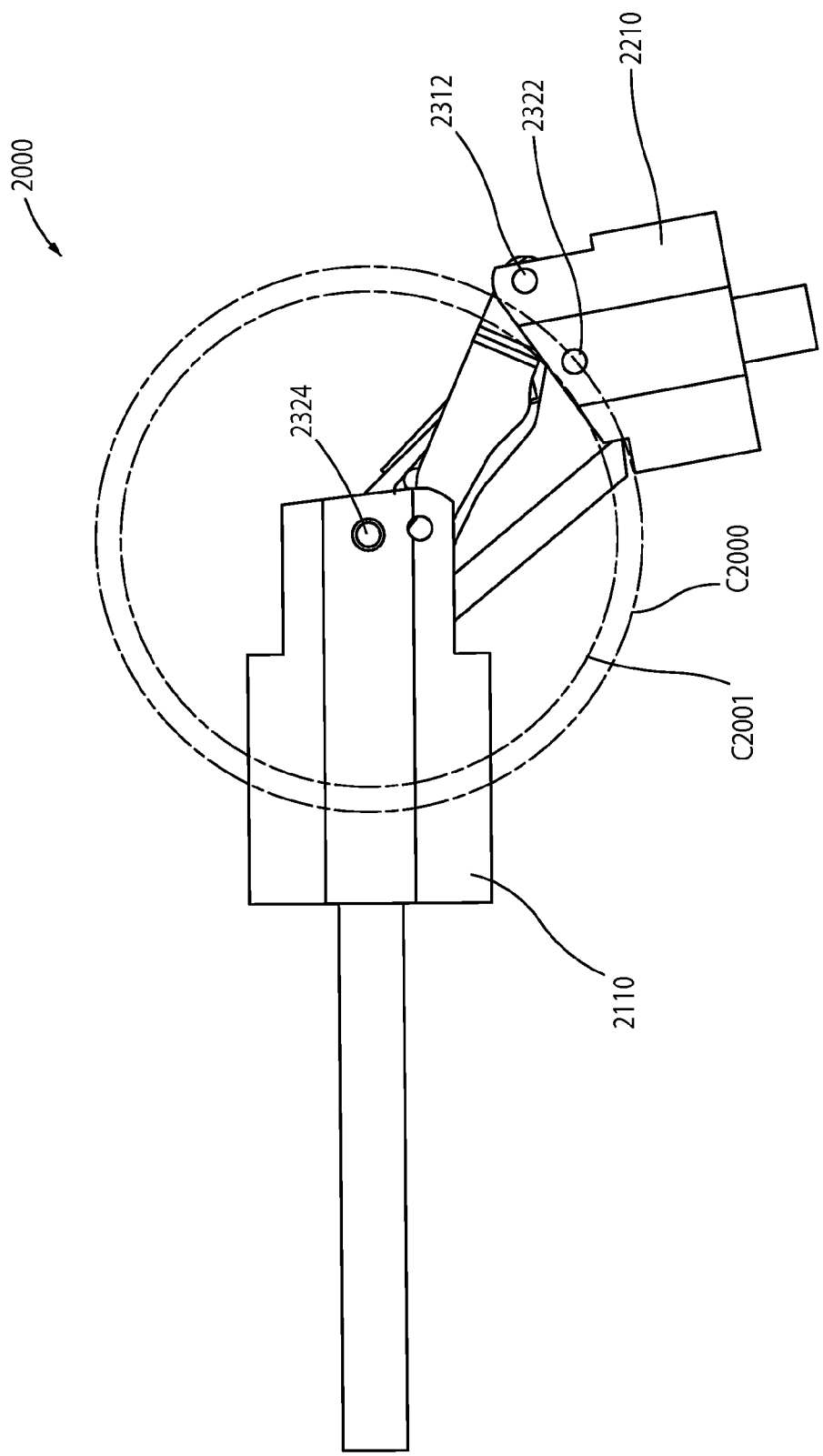
FIG. 6C is a side view of an end of the exemplary flexible wrist-type element of FIG. 5 in a second position.
Figure 6D:
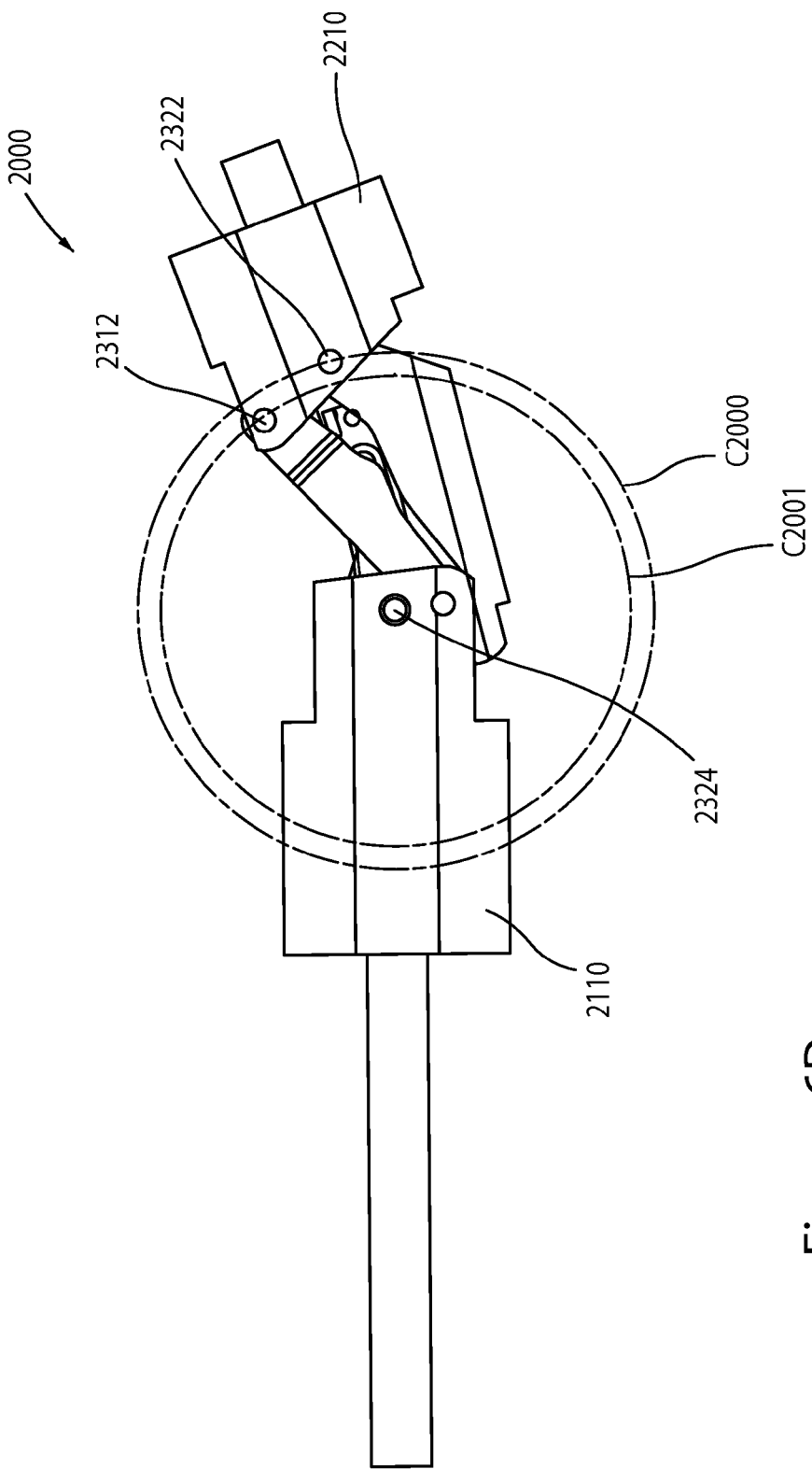
FIG. 6D is a side view of an end of the exemplary flexible wrist-type element of FIG. 5 in a third position.
Figure 6E:
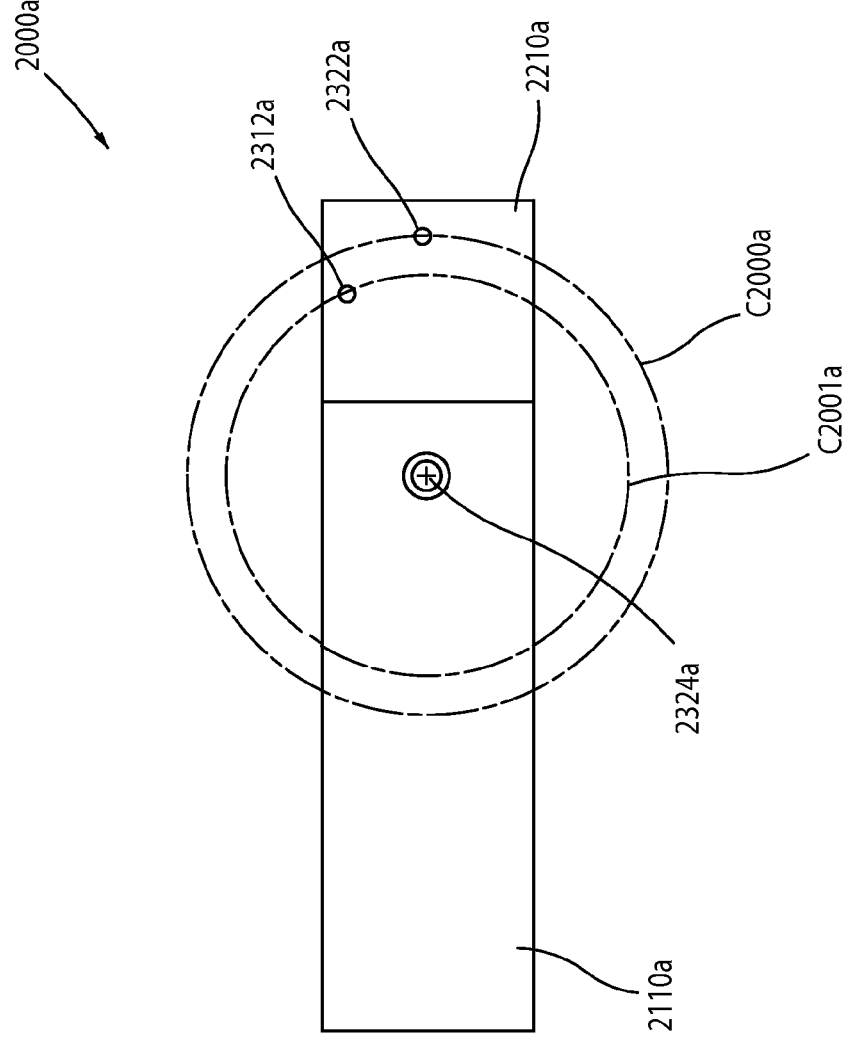
FIG. 6E is a side view of a conventional pivot system of the related art.
Figure 6F:
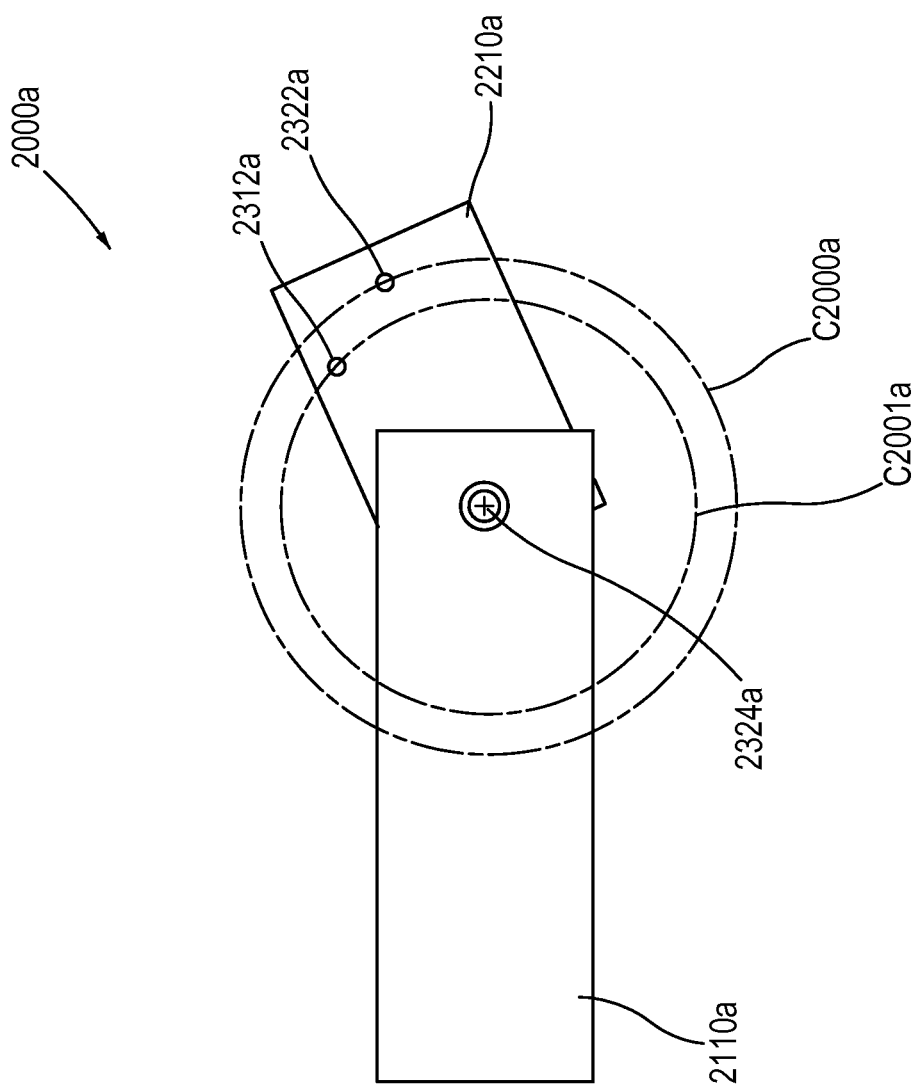
FIG. 6F is a side view of a conventional pivot system of the related art.
Figure 6G:
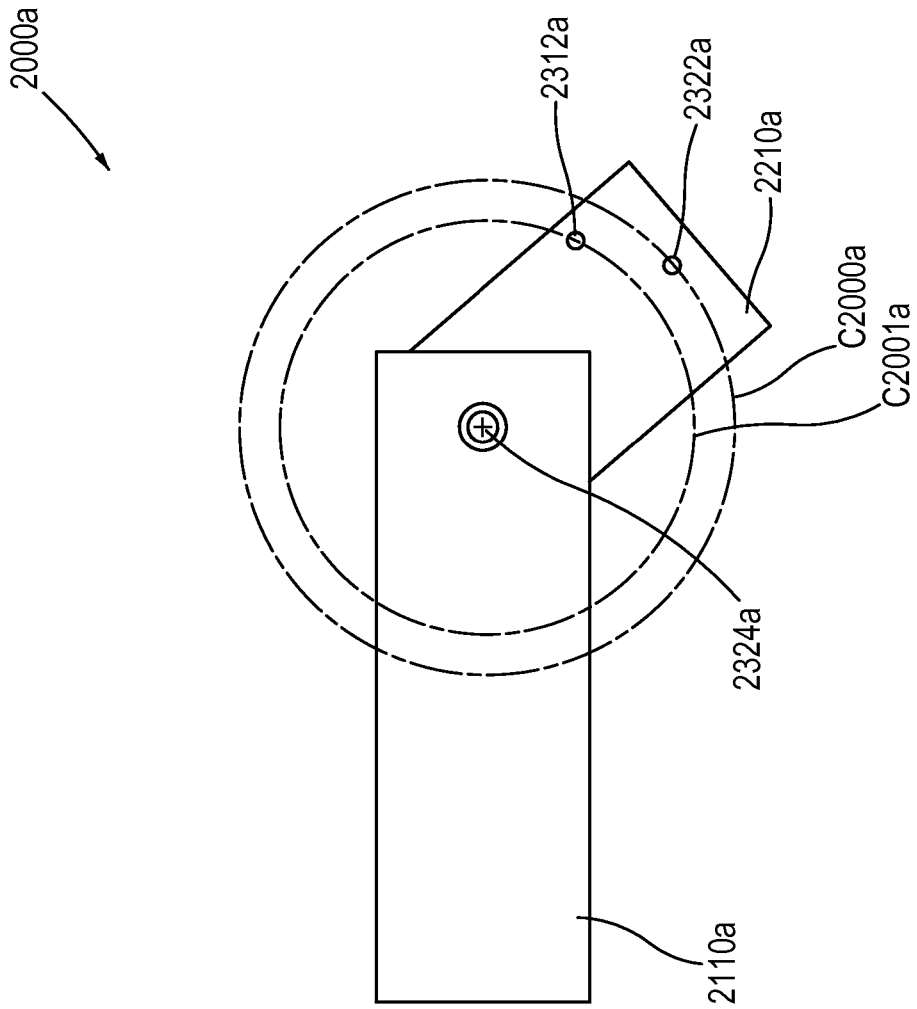
FIG. 6G is a side view of a conventional pivot system of the related art.

FIGS. 6B-6D show side views of an end of the exemplary flexible wrist-type element of FIG. 5 in three different positions to illustrate that portions of the flexible wrist-type element undergo a complex motion (e.g., a complex curve) upon bend. FIGS. 6E-6G show a pivot system 2000a of the related art for comparison. FIGS. 6B-6D show, in particular, the motion of first operational end pivot point 2312 and the second operational end pivot point 2322 relative to concentric circles C2001 and C2000 centered on second base end pivot point 2324. The choice of the first operational end pivot point 2312 and the second operational end pivot point 2322 shown in FIGS. 6B-6D merely illustrate, and, many other exemplary points on an exemplary flexible wrist-type element 2000 would likewise illustrate similar complex motion.

In FIGS. 6B and 6D, the exemplary flexible wrist-type element 2000 is shown in two different positions, in which first operational end pivot point 2312 is aligned with concentric circle C2001 and in which second operational end pivot point 2322 is aligned with concentric circle C2000. FIG. 6C shows a third position, in which first operational end pivot point 2312 is no longer aligned with concentric circle C2001. In other words, the motion of at least operational end pivot point 2312, as well as other portions of exemplary flexible wrist-type element 2000, does not correspond to a pivot about a pivot point typical of the related art.

In contrast, FIGS. 6E-6G show such a conventional pivot system 2000a of the related art. In FIGS. 6E-6G, points 2312a and 23122a correspond to the first operational end pivot point 2312 and the second operational end pivot point 2322 of FIGS. 6B-6D. Concentric circles C2001a and C2000a are centered about the main pivot point 2324 and both points 2312a and 23122a are located on the outer, pivoting portion 2210a of the conventional pivot system 2000a, as shown, for example, in FIG. 6E.

As shown in FIGS. 6E-6G, in the pivot system 2000a both points 2312a of the related art shown, and 23122a remain on their respective concentric circles C2001a and C2000a, respectively, as the conventional pivot system 2000a pivots as shown in FIGS. 6E-6G. In fact, any point on the outer portion 2210a of the conventional pivot system 2000a moves along a circular path that is centered on the main pivot point 2324a. This operation is in direct contrast to the situation shown for the exemplary flexible wrist-type element 2000 in FIGS. 6B-D, in accordance with aspects of the present invention, in which at least some of the portions of the element 2000 will undergo a more complex motion, as described above.

Second Four Bar Flexible Wrist-Type Element

Figure 9:
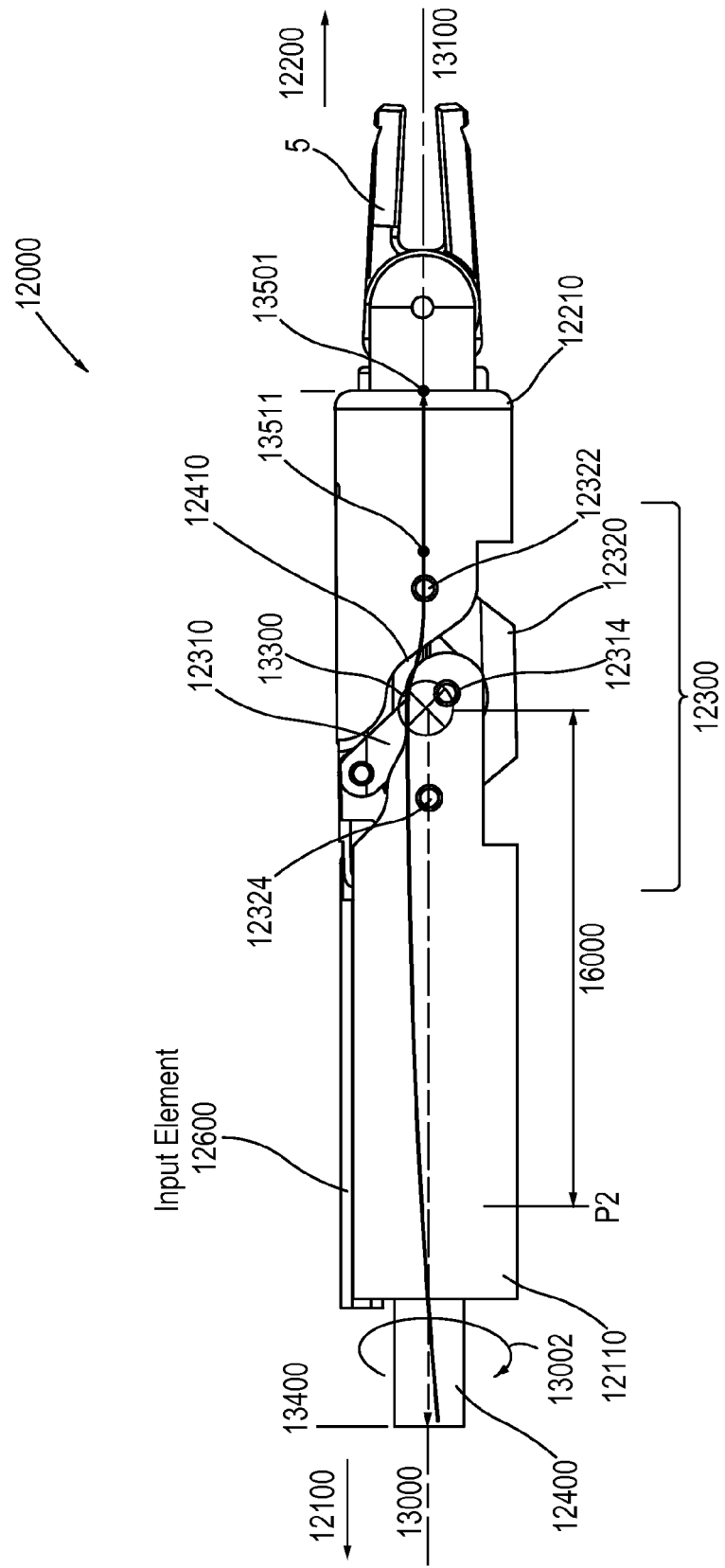
FIG. 9 is a side view of an end of an exemplary flexible wrist-type element that may be used in conjunction with the present invention in non-bending position.
Figure 10:
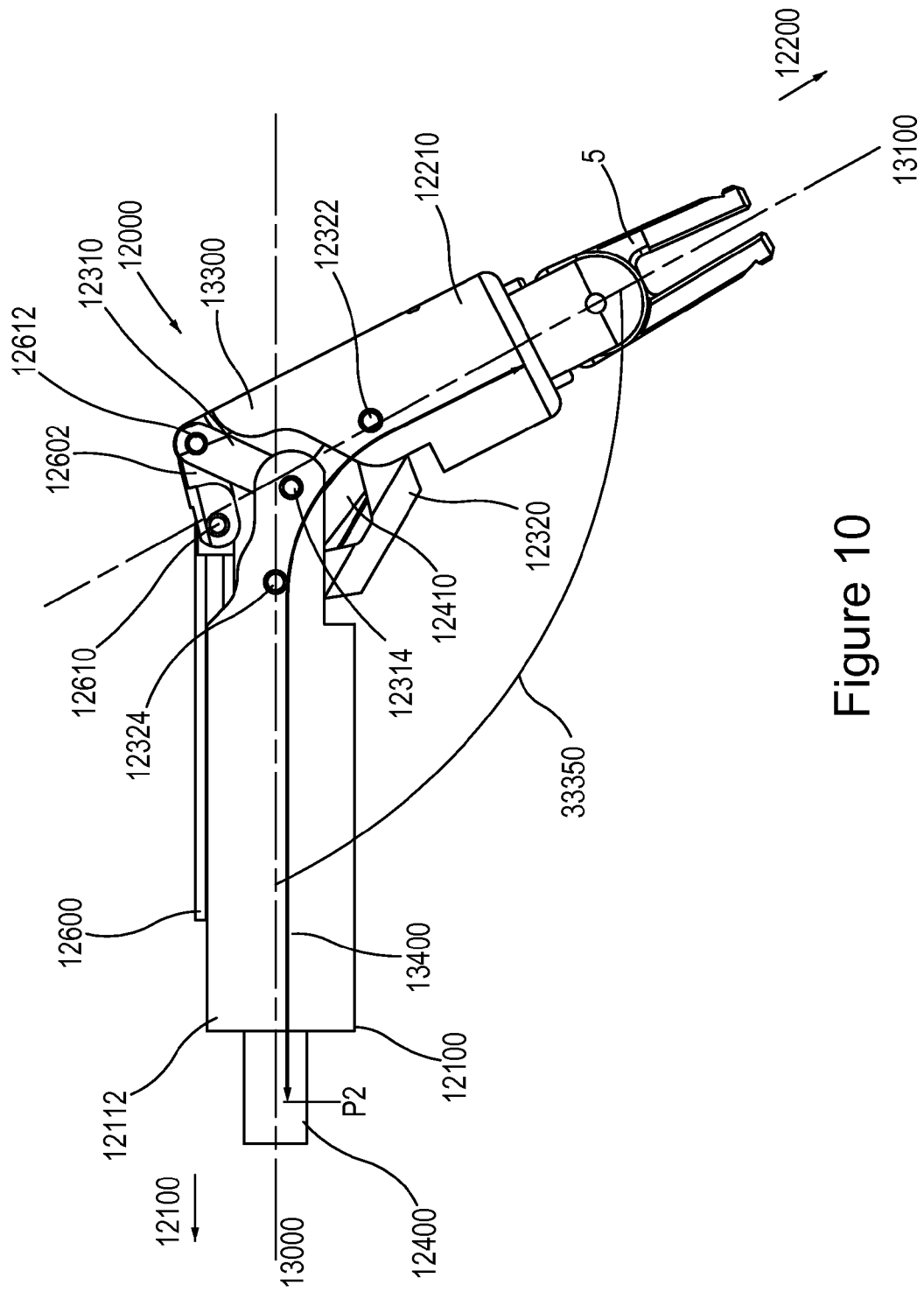
FIGS. 10 and 11 are side views of the base end 12100 and operational end 12200 illustrating relative movement during the course of operation.
Figure 11:
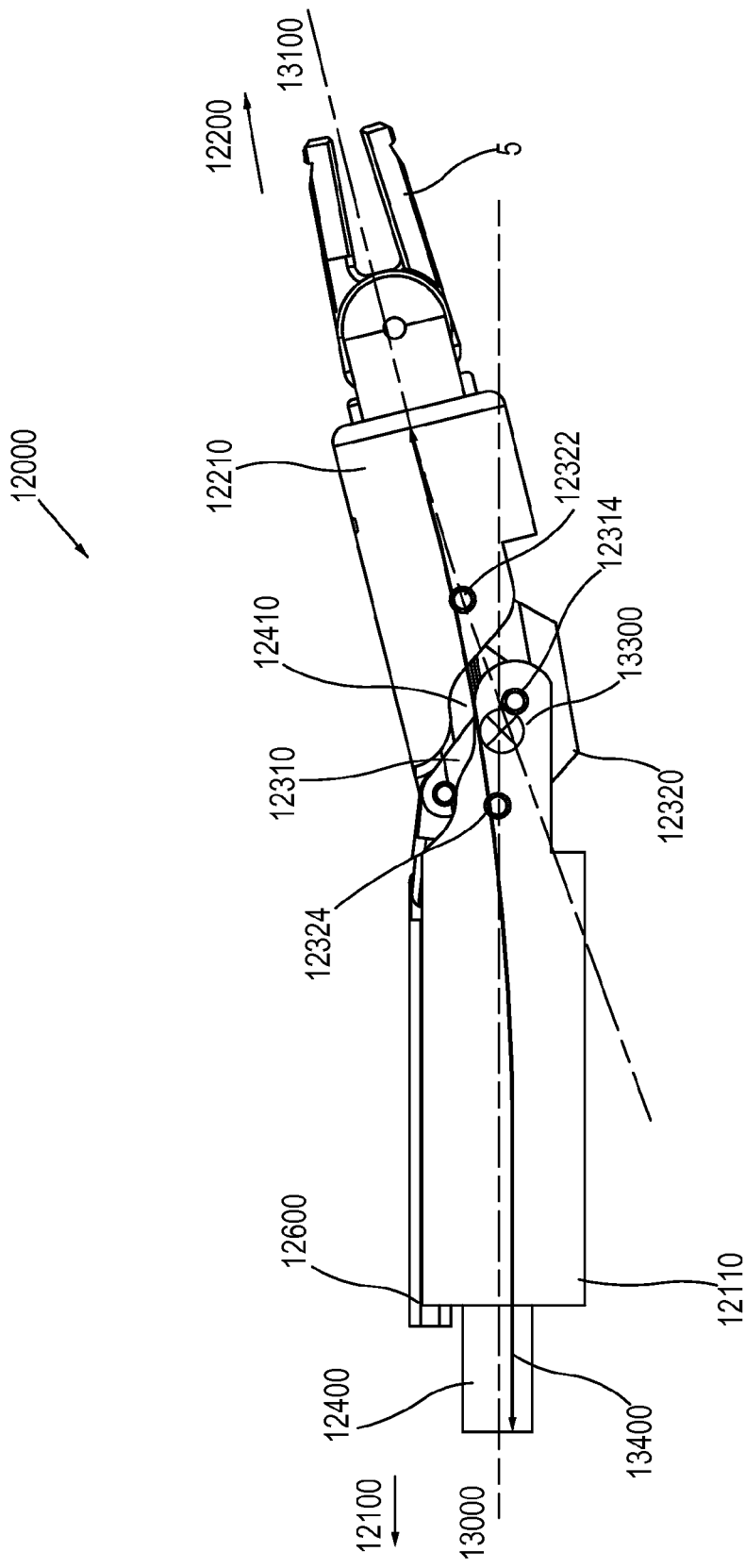
Figure 12A:
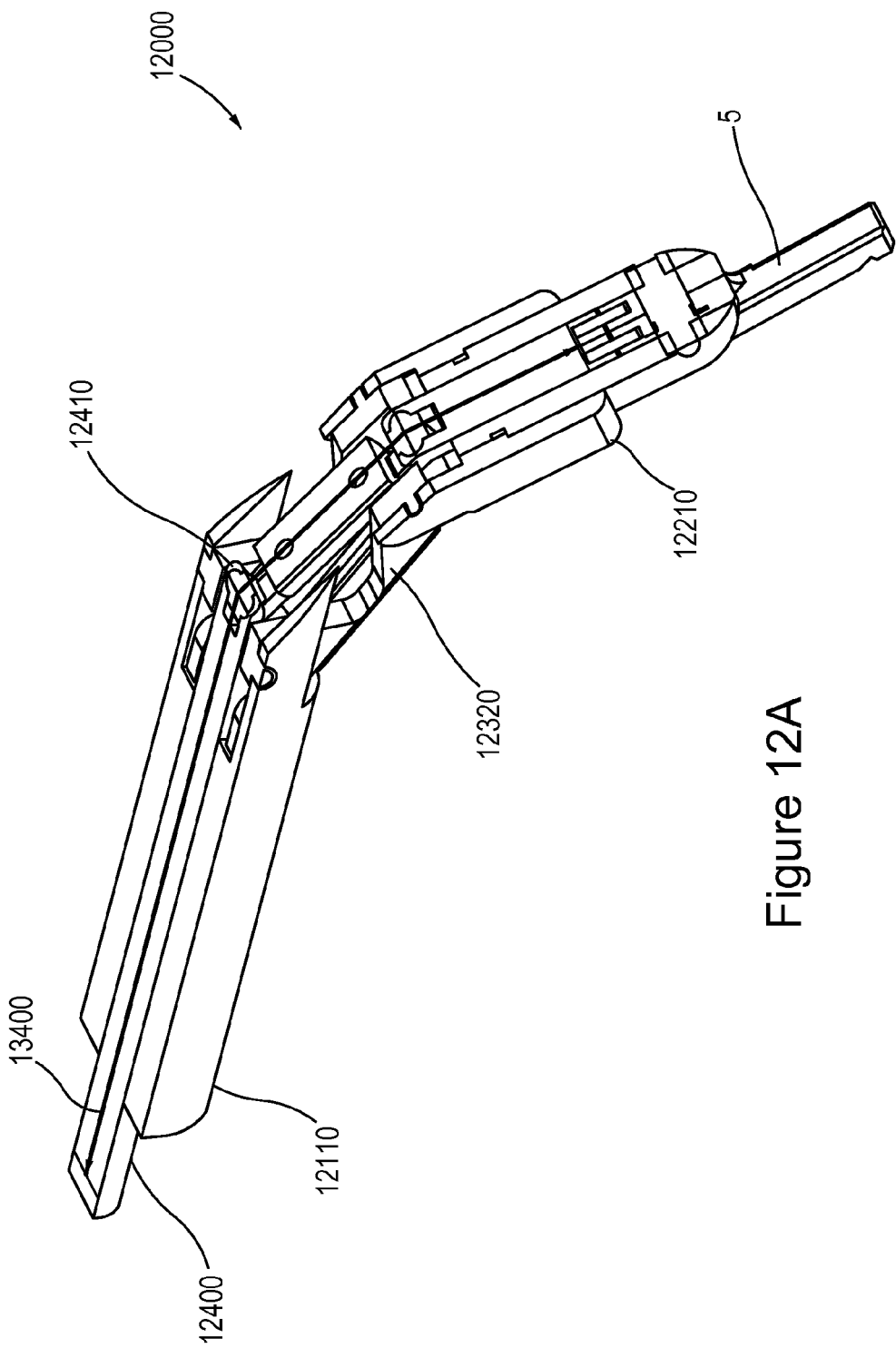
FIG. 12A is a cross-sectional view of the exemplary flexible wrist-type element of FIGS. 9-11 when it is bent.

FIG. 9 is a side view of an end of an exemplary flexible wrist-type element that may be used in conjunction with the present invention in non-bending position. FIGS. 10 and 11 are side views of the base end 12100 and operational end 12200 illustrating relative motion during the course of operation. FIG. 12A shows a cross-sectional view of the exemplary flexible wrist-type element of FIGS. 9-11 when it is bent. Such relative movement, as shown in FIGS. 10 and 11, may, for example, correspond to the Wrist Bend 174 motion shown in FIG. 4A.

As shown in FIG. 9, the exemplary flexible wrist-type element 12000 includes a base end 12100 and an operational end 12200 separated by joint assembly 12300. Generally the, base end 12100 includes a base housing 12110 and the operational end 12200 includes an operational end housing 12210. The base housing 12110 and the operational end housing 12210 may be of any suitable shape, including the shapes illustrated in FIG. 9. The base housing 12110 and the operational end housing 12210 may be monolithic, as shown in FIG. 9, or may contain any suitable number of subsidiary pieces, components and/or fixtures. A driver assembly 12400 extends from the base end 12100 to the operational end 12200 and generally allows one the remote actuation of an operational element, such as operational element 5 shown in FIG. 4A, at the operational end 12200 even when the axis meeting angle 13350 is nonzero.

More particularly, the base end 12100 of the exemplary flexible wrist-type element 12000 defines a first axis 13100 and the operational end 12200 defines a second axis 13200 that meet at an intersection point 13300. The intersection point 13300 may or may not be located on the joint assembly 12300. When the base end 12100 and operational end 12200 move relative to each other, as shown in FIGS. 9-11, the intersection point 13300 may move relative to one of, or both of, the operational end 12200 and the base end 12100. For example, FIG. 9 shows a distance 16000 between the intersection point 13300 and point P2 on the base end 12100. When the base end 12100 and operational end 12200 are moved relative to one another in a bending motion, as shown in FIG. 10, the distance between the intersection point 13300 and point P2 on the base end 12100 is increased to distance 16002. On the other hand, when the base end 12100 and operational end 12200 are moved relative to one another in another bending motion, as shown in FIG. 11, the distance between the intersection point 13300 and point P2 on the base end 12100 is decreased to distance 16002. These relative motions of the intersection point 13300 and components of the exemplary flexible wrist-type element 12000 are meant to be purely exemplary. Any other suitable relative motion of the intersection point 13300 with respect to the components of the exemplary flexible wrist-type element 12000 are included in the present invention. For example, the intersection point 13300 may move in substantially the opposite manner as shown in FIGS. 9-11. Alternatively, the intersection point 13300 may remain fixed with respect to components of the exemplary flexible wrist-type element 12000, or undergo motion along a complex curve.

The first axis 13100 and the second axis 13200 meet at the intersection point 13300 such that their intersection defines axis meeting angle 13350 (FIG. 10). The joint assembly 12300 can be used to move the base housing 12110 relative to the operational end housing 12210 such that the axis meeting angle 13350 the first axis 13100 and the second axis 13200 sweeps through a range of values. For example, the axis meeting angle 13350 may range in value from ±135°. Alternatively, in some embodiments, the axis meeting angle 13350 may range in value from as much as or more than ±90°. Although FIG. 9 shows a joint assembly 12300 that is restricted in motion such that the maximum negative value of the axis meeting angle 13350 is smaller than the maximum positive value of the axis meeting angle 13350, this is not necessarily the case. It is to be understood that the joint assembly 12300 can be constructed such that the maximum values of the axis meeting angle 13350 in both positive directions are equal, or that either one exceeds the other. The relative magnitude of the maximum values of the axis meeting angle 13350, in general, should depend on the particular application.

As shown in FIG. 9, the joint assembly 12300 includes at least two pivotable sections, first pivotable section 12310 and second pivotable section 12320. The inclusion of the first pivotable section 12310, second pivotable section 12320, base end housing 12100 and the operational end housing 12210 are the four elements that define the "4 bar" linkage of the device. The first pivotable section 12310 and second pivotable section 12320 may be of any suitable shape, including the shapes illustrated in FIG. 9. The first pivotable section 12310 and second pivotable section 12320 may be monolithic, as shown in FIG. 9, or may contain any suitable number of subsidiary pieces, components and/or fixtures. The first pivotable section 12310 and second pivotable section 12320 may cooperate with the operational end housing 12210 and the base housing 12110 to move exemplary flexible wrist-type element 12000 through a range of motion. For example, the first pivotable section 12310 and second pivotable section 12320 through the different positions, such as those shown in FIGS. 9-11. In addition, the first pivotable section 12310 and second pivotable section 12320 may be configured to be capable of imparting other types of motion to the exemplary flexible wrist-type element 12000.

The first pivotable section 12310 may further be pivotably connected to the base end housing 12110 via a first base end pivot point 12314. The second pivotable section 12320, as shown in FIG. 9, is pivotably connected to the operational end housing 12210 by a second operational end pivot point 12322. The second pivotable section 12320 may further be pivotably connected to the base end housing 12110 via a second base end pivot point 12324. As shown in FIG. 9, the second pivotable section may be disposed next to the first pivotable section 12310. Alternatively, the second pivotable section 12320 and the first pivotable section 12310 may have one of a number of suitable relationships, including: being placed side-by-side, placed such that one pivotable section is nested within the other or other suitable relationships. Although only two pivot points are shown for each of the first pivotable section 12310 and second pivotable section 12320 in FIG. 9, it is to be understood that the number of pivot points is not limited to that number. Any suitable number of pivot points is possible and additional pivot points may provide additional range of motion to the joint assembly 12300.

FIG. 9 also shows an input element 12600 that is pivotably coupled to the first pivotable section 12310 via an input element pivotable section 12602. More specifically, the input element pivotable section 12602 is pivotably coupled to the input element 12600 via pivotable coupling 12610 and to the first pivotable section 12310 and the operational end housing 12210 via pivotable coupling 12612. Base housing 12110 further includes a track 12112 in which the Input element 12600 is slidably inserted such that it slides back and forth along the first longitudinal axis 13000 when actuated by, for example, the control portion 50.

Sweeping the axis meeting angle 13350 is accomplished using the various components of the joint assembly 12300. Sliding Input element 12600 along the first longitudinal axis 13000 causes the input element pivotable section 12602 to push both the first pivotable section 12310 and the operational end housing 12210 via pivotable coupling 12612 such that the first pivotable section 12310 pivots about first base end pivot point 12314 (as shown in FIGS. 9-11). This pivoting causes the operational end housing 12210 to move relative to the base end housing 12110. Such motion of the operational end housing 12210 relative to the base end housing 12110 causes a relative movement of the first 13000 and second 13100 longitudinal axes sweeping through values of the axis meeting angle 13350 (e.g., as shown in FIG. 4C).

Generally, the driver assembly 12400 establishes a mechanical link between the base end 12100 and the operational end 12200. The driver assembly 12400 is best shown in FIG. 12. As discussed above, the operational end 12200 may include an operational element, such as, for example, the operational element 5 shown in FIG. 4A, that can be actuated by the driver assembly 12400. For example, control unit 1200 (FIG. 12) may be coupled to the driver assembly 12400 via hydraulic actuators in the manner described in the context of FIG. 4A. In such a configuration, a user's motions while operating the control 12000 may be transferred hydraulically, for example, to the driver assembly 12400. The driver assembly 12400, then, may transfer the same motions (or amplified version of such motions) mechanically to the operational element 5. In this way the driver assembly 12400 may act as a mechanical conduit between the control assembly 1200 and the operational element 5. Such a configuration may be used to perform each of the micro motions shown in FIG. 4A. For example, actuation of the control unit 1200 may cause the driver assembly 12400 to cause the operational element 5 to perform one or more of the Tip Grasp 176, Tip Rotation 175, Wrist Bend 174 or Forearm Rotation 173 motions shown in FIG. 4A.

The driver assembly 12400 may, for example, be able to transfer mechanical motion to, actuate or mechanically communicate with the operational element 5 such that the operational element 5 can, for example, perform some or all of the micro motions shown in FIG. 4A. For example, the Tip Grasp 176 motion may be actuated by moving the driver assembly 12400 along direction 13001, a direction that is co-incident and co-linear with the path length 13400 made by the driver assembly 12400 throughout the exemplary flexible wrist-type element 12000. The Tip Rotation 175 motion, for example, may be actuated by rotating the driver assembly 12400 along rotational direction 13002 with respect to the base end housing 12110 and the operational end housing 12210.

Figure 16:
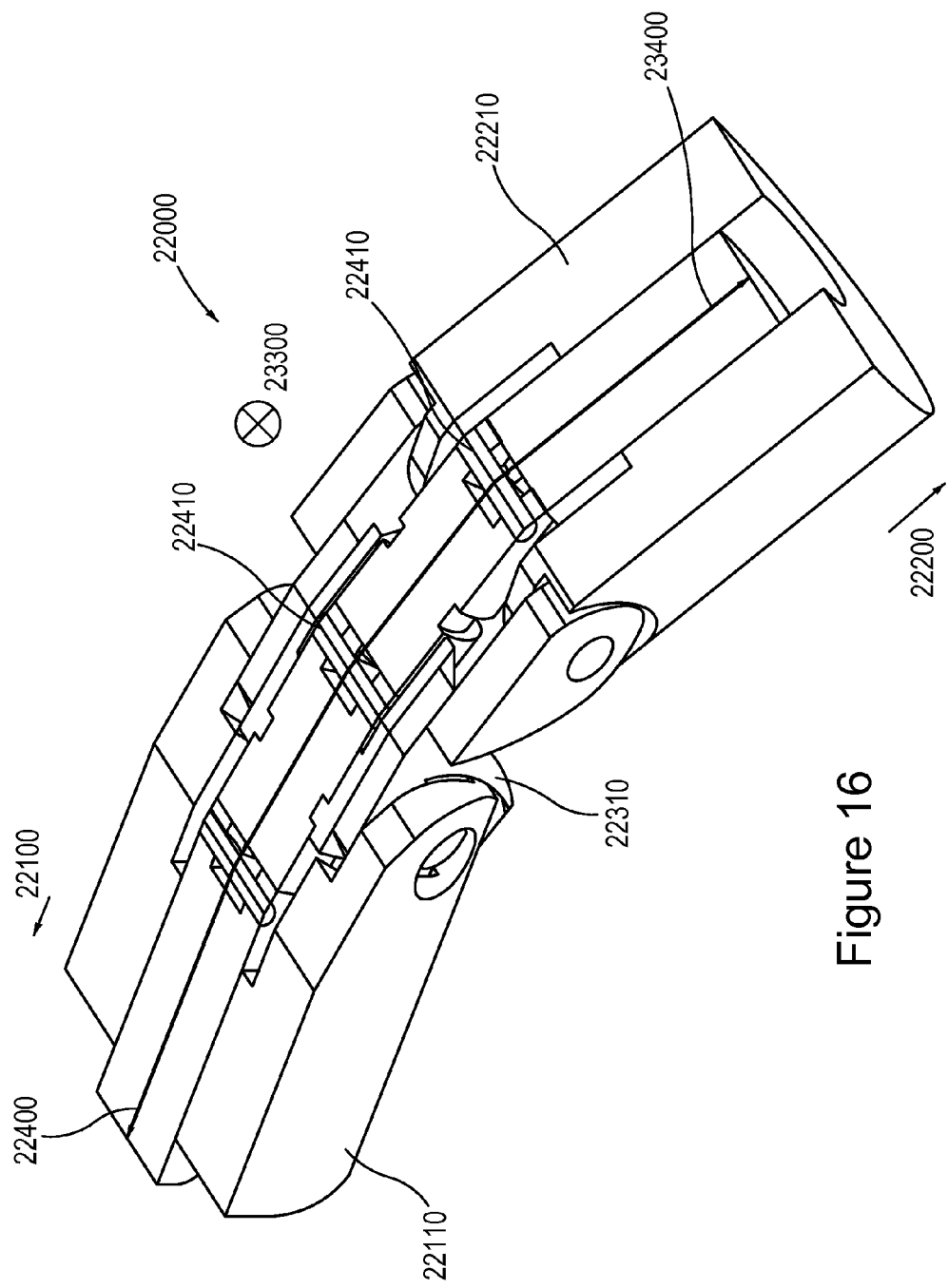
FIG. 16 is a cross-sectional view of the exemplary flexible wrist-type element of FIGS. 13-15 when it is bent.

The driver assembly 12400 may include, for example, one or more u-joints 12410, as shown in FIGS. 5 and 16 in order to, among other things, transfer mechanical motion to, actuate or mechanically communicate with the operational element 5. U-joints 12410 may, for example, be similar to the U-joint 95 shown in FIG. 4D. The u-joints 12410 may allow the driver assembly 12400 to maintain mechanical communication between a base end section 12420 and an operational end section 12430 of the driver assembly 12400 even as the exemplary flexible wrist-type element 12000 is bent, as shown, for example, in FIG. 10. Maintaining mechanical communication in this way enables the driver assembly 12400 to actuate the operational element 5 in the manner described above even when the joint assembly 12300 is bent a Wrist Bend 174 motion, as shown, for example, in FIG. 10. The driver assembly 12400 could also or alternatively be fashioned from other flexible mechanical devices such as, for example, push-pull cables or other cables. This wrist structure, and any of the wrist structures discussed herein could be used to maintain even path length for non-driving elements, such as wires, hoses, etc.

Generally the joint assembly 12300 is constructed so that the path length 13400 remains constant during a Wrist Bend 174 (FIG. 4A, FIGS. 9-11). Keeping the path length 13400 constant during such a bend allows the driver assembly 12400 to actuate the operational element 5 motion (e.g., Tip Grasp 176) motion regardless of the relative positions of the base end housing 12100 and the operational end housing 12210. The path length 13400 may be kept constant using a variety of configurations. As shown in FIGS. 9-11, one exemplary configuration that keeps the path length constant is to construct the first pivotable section 12310 and the second pivotable section 12320 such that there is an opening 12330 large enough to allow the driver assembly 12400 to move laterally or to "bulge" out of the joint assembly 12300, as shown in FIG. 10, when the exemplary flexible wrist-type element 12000 exercises a Wrist Bend 174 motion (as shown in FIG. 4A and FIGS. 9-11).

Figure 12B:
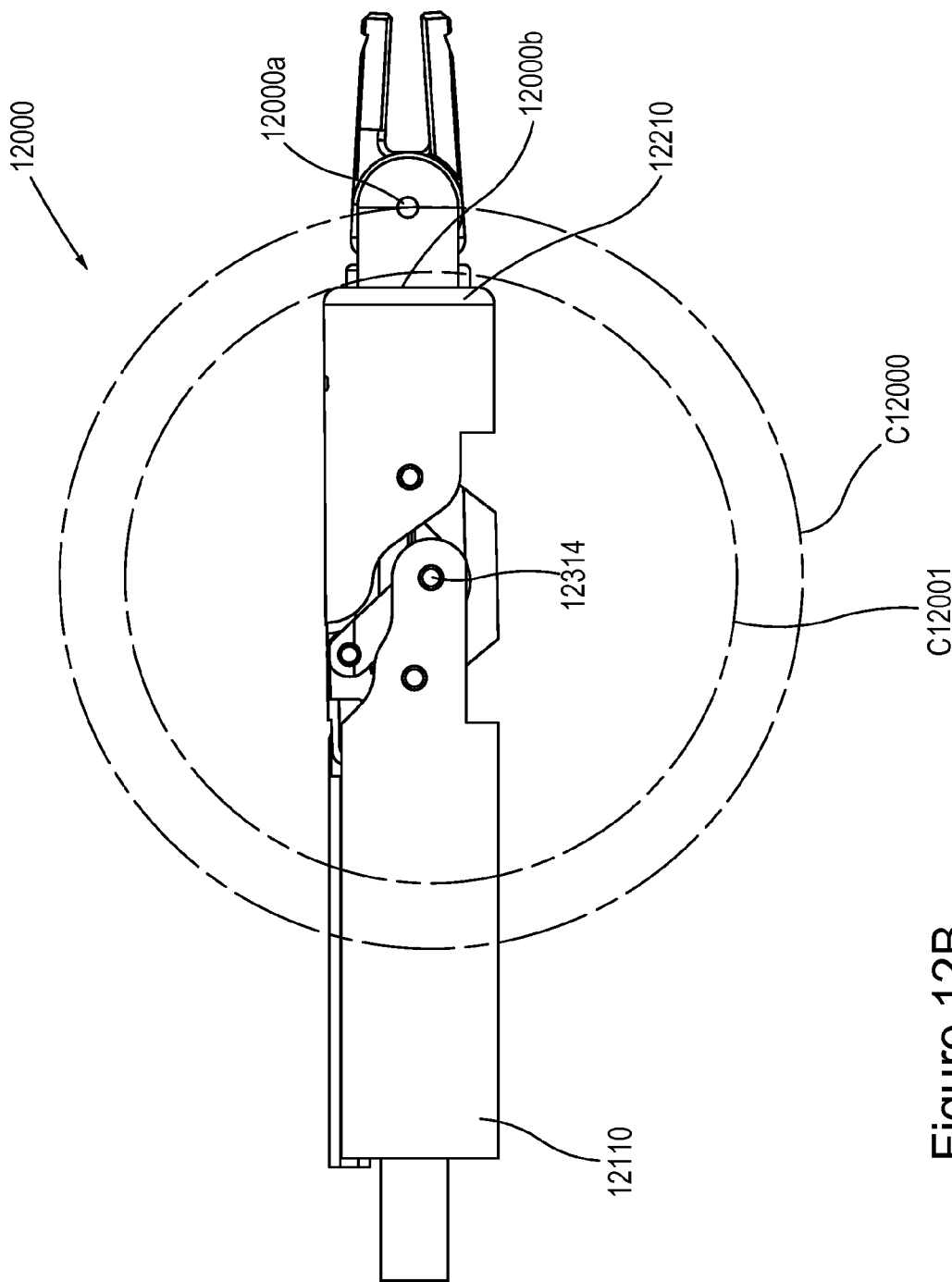
FIG. 12B is a side view of an end of the exemplary flexible wrist-type element of FIGS. 9-11 in a first position.
Figure 12C:
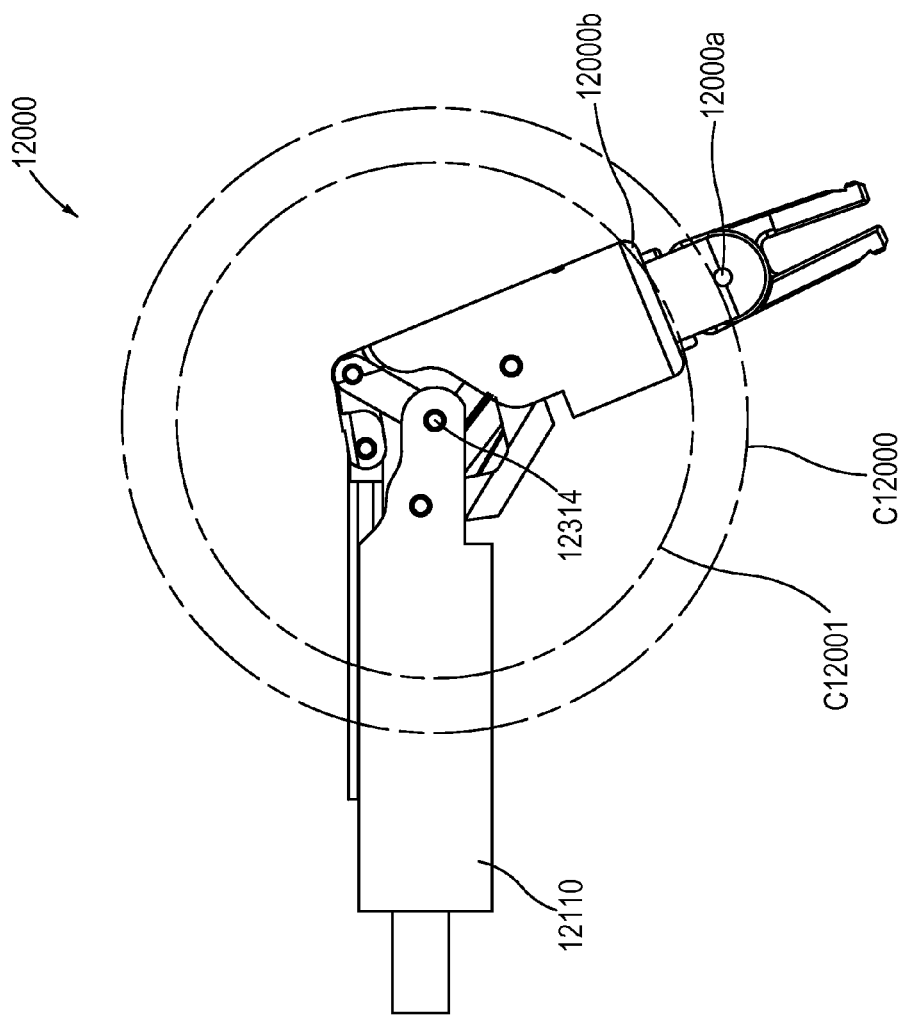
FIG. 12C is a side view of an end of the exemplary flexible wrist-type element of FIGS. 9-11 in a second position.
Figure 12D:
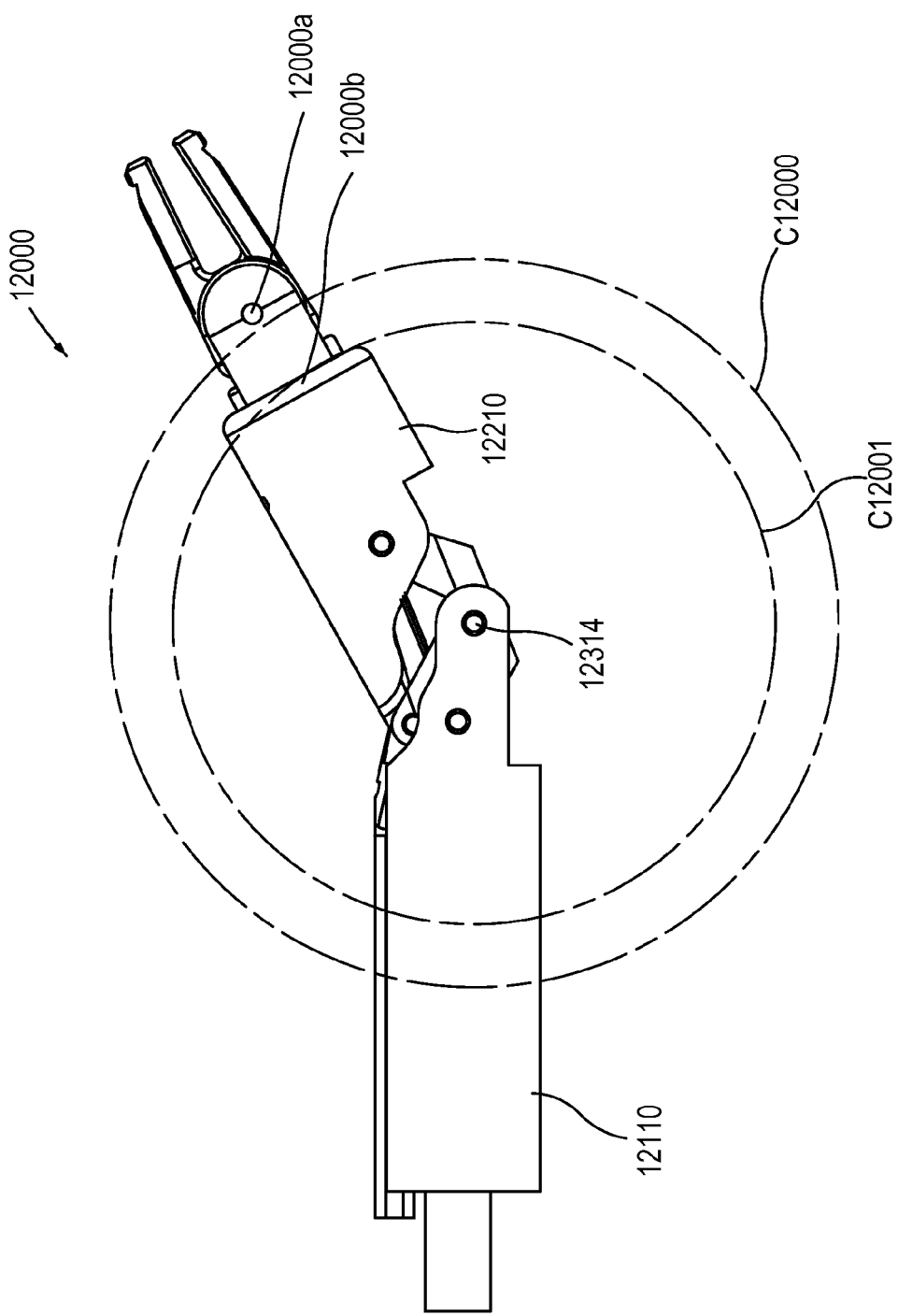
FIG. 12D is a side view of an end of the exemplary flexible wrist-type element of FIGS. 9-11 in a third position.

FIGS. 12B-12D show side views of an end of the exemplary flexible wrist-type element of FIG. 9, in three different positions to illustrate that portions of the flexible wrist-type element undergo a complex motion (e.g., a complex curve) upon bend. FIGS. 12B-12D show, in particular, the motion of point 12000B and the point 12000A relative to concentric circles C2001 and C2000 centered on second base end pivot point 2324. The choice of the point 12000B and the point 12000A is illustrate, and, many other exemplary points on exemplary flexible wrist-type element 12000 may be used to similarly illustrate the complex motion.

In FIG. 12B, point 12000B is not shown as aligned with concentric circle C2001, but point 12000A is shown as aligned with concentric circle C2000. When the exemplary flexible wrist-type element 12000 is moved to the position shown in FIG. 12C, point 12000B as shown becomes aligned with concentric circle C2001, and point 12000A is shown as not aligned with concentric circle C2000. When the exemplary flexible wrist-type element 12000 is moved to the position shown in FIG. 12C, point 12000B is not shown as aligned with concentric circle C2001, and point 12000A is not shown as aligned with concentric circle C2000. In other words, the motion of points 12000A and 12000B, as well as other portions of exemplary flexible wrist-type element 12000, does not correspond to a pivot about a pivot point in the related art. This motion can be directly contrasted with that shown for the related art pivot system 2000a in FIGS. 6E-6G and discussed above, for example.

U-Joint Wrist-Type Element

Figure 13:
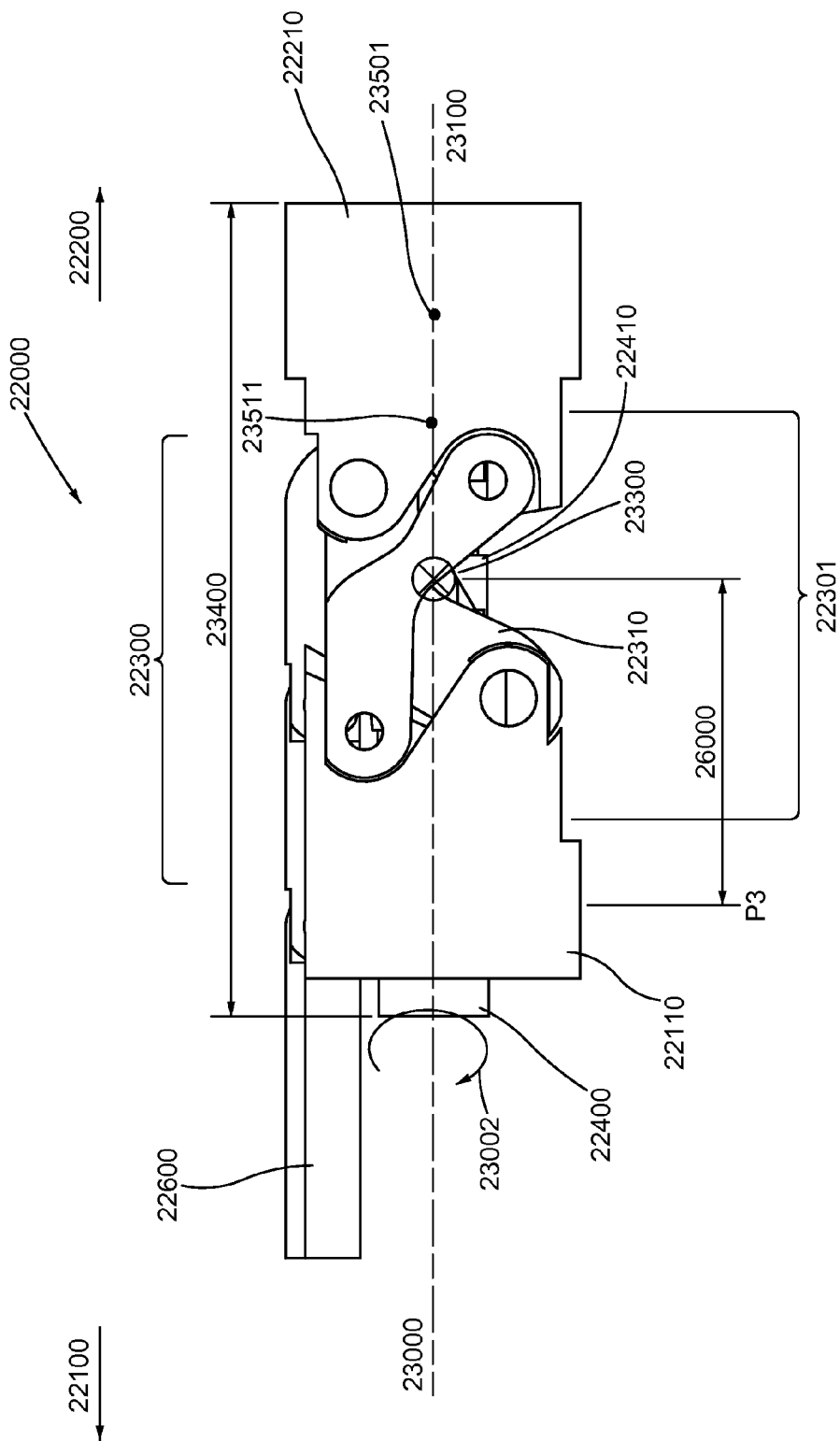
FIG. 13 is a side view of an end of an exemplary flexible wrist-type element that may be used in conjunction with the present invention in non-bending position.
Figure 14:
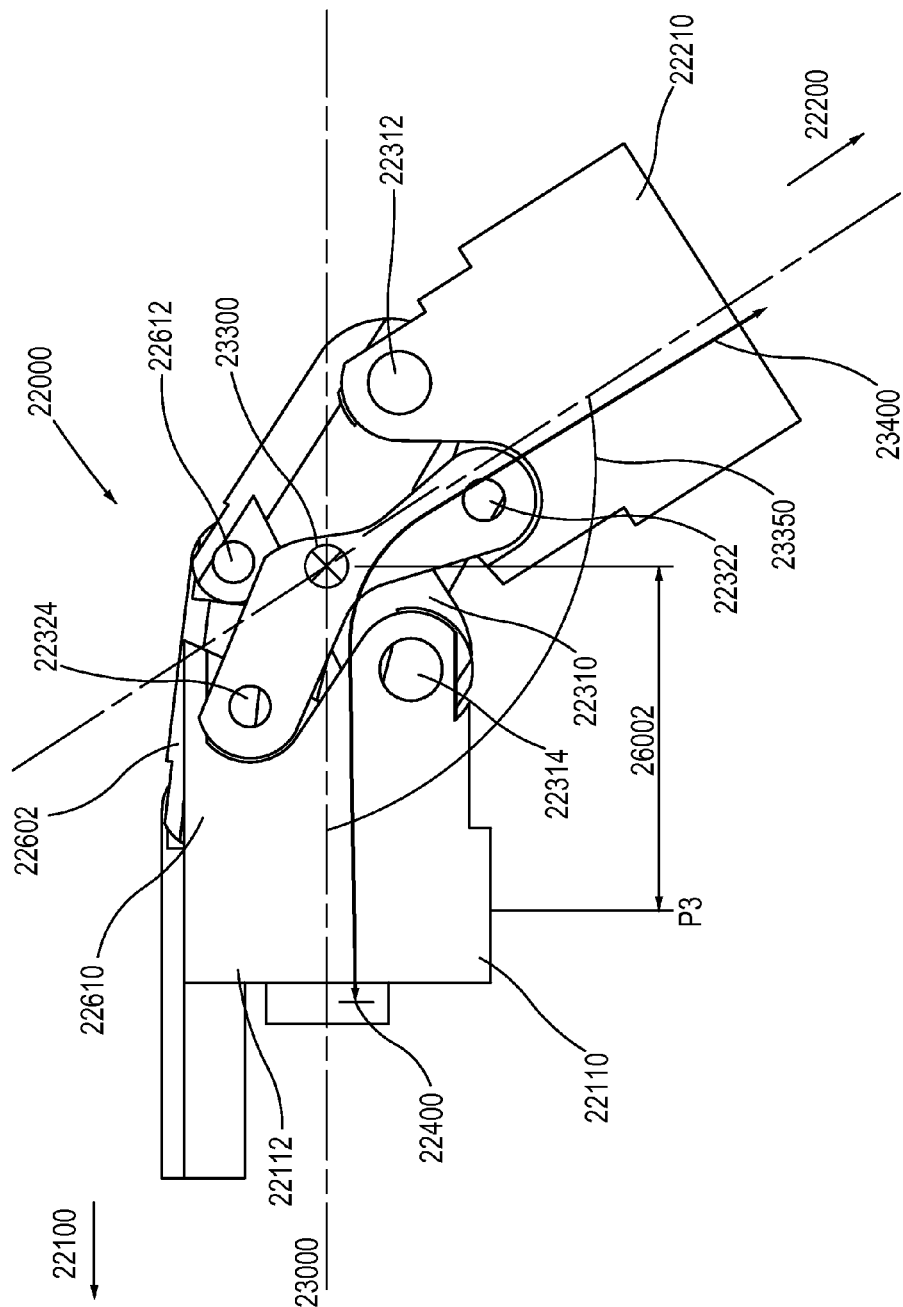
FIGS. 14 and 15 are side views of the base end 22100 and operational end 22200 illustrating relative motion during the course of operation.
Figure 15:
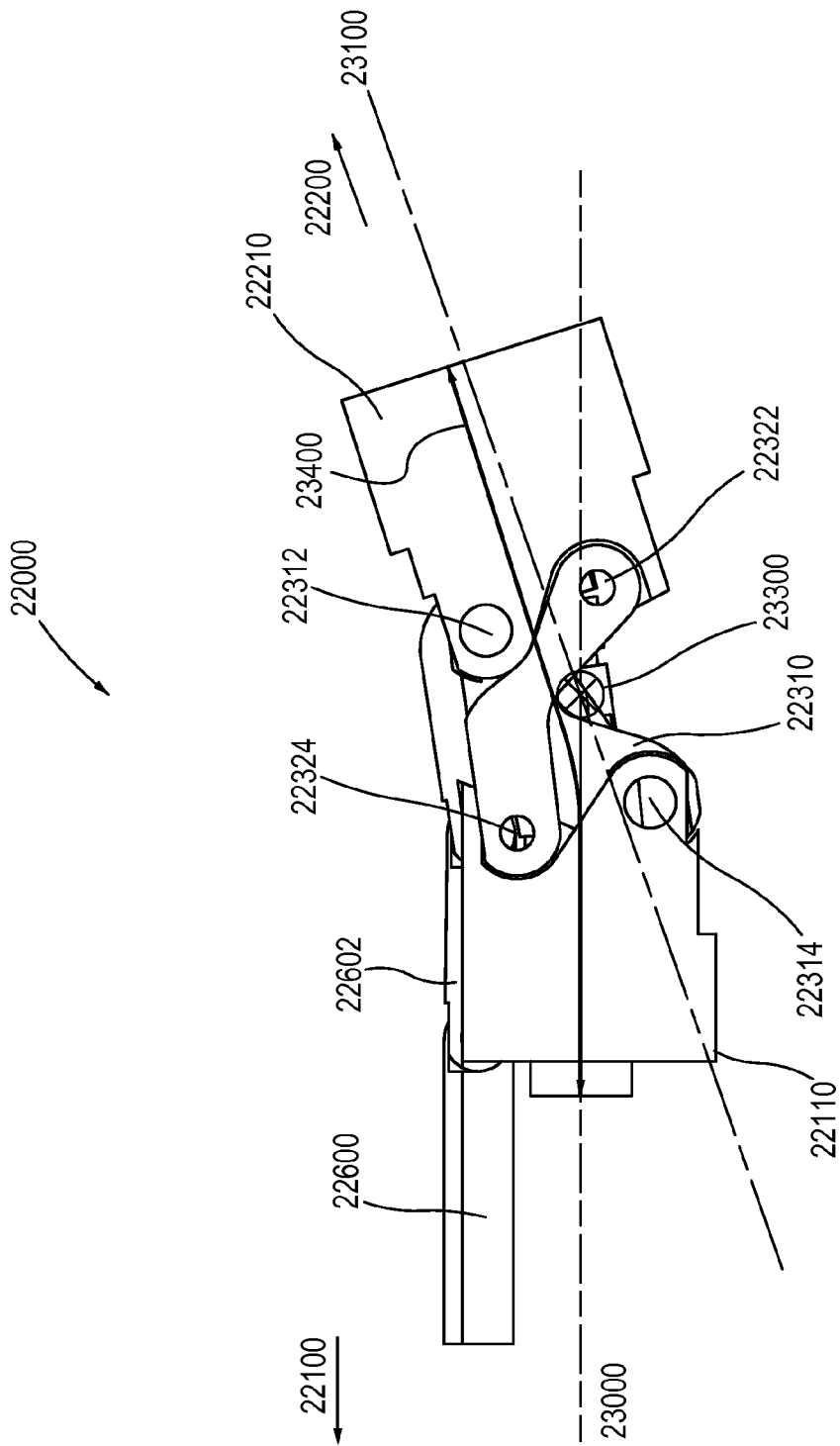

FIG. 13 is a side view of an end of an exemplary flexible wrist-type element that may be used in conjunction with the present invention in non-bending position. FIGS. 14 and 15 are side views of the base end 22100 and operational end 22200 illustrating relative motion during the course of operation. FIG. 16 shows a cross-sectional view of the exemplary flexible wrist-type element of FIGS. 13-15 when it is bent. Such relative movement, as shown in FIGS. 14 and 15, may, for example, correspond to the Wrist Bend 174 motion shown in FIG. 4A.

As shown in FIG. 13, the exemplary flexible wrist-type element 22000 includes a base end 22100 and an operational end 22200 separated by joint assembly 22300. Generally the, base end 22100 includes a base housing 22110 and the operational end 22200 includes an operational end housing 22210. The base housing 22110 and the operational end housing 22210 may be of any suitable shape, including the shapes illustrated in FIG. 13. The base housing 22110 and the operational end housing 22210 may be monolithic, as shown in FIG. 13, or may contain any suitable number of subsidiary pieces, components and/or fixtures. A driver assembly 22400 extends from the base end 22100 to the operational end 22200 and generally allows one the remote actuation of an operational element, such as operational element 5 shown in FIG. 4A, at the operational end 22200 even when the axis meeting angle 23350 is nonzero.

More particularly, the base end 22100 of the exemplary flexible wrist-type element 22000 defines a first axis 23100 and the operational end 22200 defines a second axis 23200 that meet at an intersection point 23300. The intersection point 23300 may or may not be located on the joint assembly 22300. When the base end 22100 and operational end 22200 move relative to each other, as shown in FIGS. 13-15, the intersection point 23300 may move relative to one of, or both of, the operational end 22200 and the base end 22100. For example, FIG. 13 shows a distance 26000 between the intersection point 23300 and point P3 on the base end 22100. When the base end 22100 and operational end 22200 are moved relative to one another in a bending motion, as shown in FIG. 14, the distance between the intersection point 23300 and point P3 on the base end 22100 is increased to distance 26002. On the other hand, when the base end 22100 and operational end 22200 are moved relative to one another in another bending motion, as shown in FIG. 15, the distance between the intersection point 23300 and point P3 on the base end 22100 is decreased to distance 26002. These relative motions of the intersection point 23300 and components of the exemplary flexible wrist-type element 22000 are meant to be purely exemplary. Any other suitable relative motion of the intersection point 23300 with respect to the components of the exemplary flexible wrist-type element 22000 are included in the present invention. For example, the intersection point 23300 may move in substantially the opposite manner as shown in FIGS. 13-15. Alternatively, the intersection point 23300 may remain fixed with respect to components of the exemplary flexible wrist-type element 22000, or undergo motion along a complex curve.

The first axis 23100 and the second axis 23200 meet at the intersection point 23300 such that their intersection defines axis meeting angle 23350 (FIG. 14). The joint assembly 22300 can be used to move the base housing 22110 relative to the operational end housing 22210 such that the axis meeting angle 23350 the first axis 23100 and the second axis 23200 sweeps through a range of values. For example, the axis meeting angle 23350 may range in value from ±135°. Alternatively, in some embodiments, the axis meeting angle 23350 may range in value from as much as or more than ±90°. Although FIG. 13 shows a joint assembly 22300 that is restricted in motion such that the maximum negative value of the axis meeting angle 23350 is smaller than the maximum positive value of the axis meeting angle 23350, this is not necessarily the case. It is to be understood that the joint assembly 22300 can be constructed such that the maximum values of the axis meeting angle 23350 in both positive directions are equal, or that either one exceeds the other. The relative magnitude of the maximum values of the axis meeting angle 23350, in general, should depend on the particular application.

As shown in FIG. 13, the joint assembly 22300 includes at least two pivotable sections, first pivotable section 22310 and second pivotable section 22320. The first pivotable section 22310 and second pivotable section 22320 may be of any suitable shape, including the shapes illustrated in FIG. 13. The first pivotable section 22310 and second pivotable section 22320 may be monolithic, as shown in FIG. 13, or may contain any suitable number of subsidiary pieces, components and/or fixtures. The first pivotable section 22310 and second pivotable section 22320 may cooperate with the operational end housing 22210 and the base housing 22110 to move exemplary flexible wrist-type element 22000 through a range of motion. For example, the first pivotable section 22310 and second pivotable section 22320 through axis meeting angle 23350 values, such as those shown in FIGS. 13-15. In addition, the first pivotable section 22310 and second pivotable section 22320 may be configured to be capable of imparting other types of motion to the exemplary flexible wrist-type element 22000.

The first pivotable section 22310 may further be pivotably connected to the base end housing 22110 via a first base end pivot point 22314. In addition, as shown in FIG. 13, the joint assembly 22300 may further include a second pivotable section 22320. The second pivotable section 22320, as shown in FIG. 13, is pivotably connected to the operational end housing 22210 by a second operational end pivot point 22322. The second pivotable section 22320 may further be pivotably connected to the base end housing 22110 via a second base end pivot point 22324. As shown in FIG. 13, the second pivotable section may be disposed next to the first pivotable section 22310. Alternatively, the second pivotable section 22320 and the first pivotable section 22310 may have one of a number of suitable relationships, including: being placed side-by-side, placed such that one pivotable section is nested within the other or other suitable relationships. Although only two pivot points are shown for each of the first pivotable section 22310 and second pivotable section 22320 in FIG. 13, it is to be understood that the number of pivot points is not limited to that number. Any suitable number of pivot points is possible and additional pivot points may provide additional range of motion to the joint assembly 22300.

FIGS. 13 and 14 also show an input element 22600 that is pivotably coupled to the first pivotable section 22310 via an input element pivotable section 22602. More specifically, the input element pivotable section 22602 is pivotably coupled to the input element 22600 via pivotable coupling 22610 and to the first pivotable section 22310 via pivotable coupling 22612. The first pivotable section 22310 is further pivotably coupled to the operational end housing 22210 via first operational end pivot point 22312. Base housing 22110 further includes a track 22112 in which the Input element 22600 is slidably inserted such that it slides back and forth along the first longitudinal axis 23000 when actuated by, for example, the control portion 50.

Sweeping the axis meeting angle 23350 is accomplished using the various components of the joint assembly 22300. Sliding Input element 22600 along the first longitudinal axis 23000 causes the input element pivotable section 22602 to push both the first pivotable section 22310 via pivotable coupling 22612 such that the first pivotable section 22310 pivots about first base end pivot point 22314 (as shown in FIGS. 13-14). This further causes the operational end housing 22210 to pivot relative to the base end housing 22110 via first operational end pivot point 22312. This pivoting causes the operational end housing 22210, and therefore, to move relative to the base end housing 22110. Such motion of the operational end housing 22210 relative to the base end housing 22110 causes a relative movement of the first 23000 and second 23100 longitudinal axes sweeping through values of the axis meeting angle 23350 (e.g., as shown in FIG. 4C).

Generally, the driver assembly 22400 establishes a mechanical link between the base end 22100 and the operational end 22200. The driver assembly 22400 is best shown in FIG. 16. As discussed above, the operational end 22200 may include an operational element, such as, for example, the operational element 5 shown in FIG. 4A, that can be actuated by the driver assembly 22400. For example, control unit 2200 (FIG. 16) may be coupled to the driver assembly 22400 via hydraulic actuators in the manner described in the context of FIG. 4A. In such a configuration, a user's motions while operating the control 22000 may be transferred hydraulically, for example, to the driver assembly 22400. The driver assembly 22400, then, may transfer the same motions (or amplified version of such motions) mechanically to the operational element 5. In this way the driver assembly 22400 may act as a mechanical conduit between the control assembly 2200 and the operational element 5. Such a configuration may be used to perform each of the micro motions shown in FIG. 4A. For example, actuation of the control unit 2200 may cause the driver assembly 22400 to cause the operational element 5 to perform one or more of the Tip Grasp 176, Tip Rotation 175, Wrist Bend 174 or Forearm Rotation 173 motions shown in FIG. 4A.

The driver assembly 22400 may, for example, be able to transfer mechanical motion to, actuate or mechanically communicate with the operational element 5 such that the operational element 5 can, for example, perform some or all of the micro motions shown in FIG. 4A. For example, the Tip Grasp 176 motion may be actuated by moving the driver assembly 22400 along direction 23001, a direction that is co-incident and co-linear with the path length 23400 made by the driver assembly 22400 throughout the exemplary flexible wrist-type element 22000. The Tip Rotation 175 motion, for example, may be actuated by rotating the driver assembly 22400 along rotational direction 23002 with respect to the base end housing 22110 and the operational end housing 22210.

The driver assembly 22400 may include, for example, one or more u-joints 22410, as shown in FIGS. 5 and 26 in order to, among other things, transfer mechanical motion to, actuate or mechanically communicate with the operational element 5. U-joints 22410 may, for example, be similar to the U-joint 95 shown in FIG. 4D. The u-joints 22410 may allow the driver assembly 22400 to maintain mechanical communication between a base end section 22420 and an operational end section 22430 of the driver assembly 22400 even as the exemplary flexible wrist-type element 22000 is bent, as shown, for example, in FIG. 14. Maintaining mechanical communication in this way enables the driver assembly 22400 to actuate the operational element 5 in the manner described above even when the joint assembly 22300 is bent a Wrist Bend 174 motion, as shown, for example, in FIG. 14. The driver assembly 22400 could also or alternatively be fashioned from other flexible mechanical devices such as, for example, push-pull cables or other cables. This wrist structure, and any of the wrist structures discussed herein could be used to maintain even path length for non-driving elements, such as wires, hoses, etc.

Generally the joint assembly 22300 is constructed so that the path length 23400 remains constant during a Wrist Bend 174 (FIG. 4A, FIGS. 13-15). Keeping the path length 23400 constant during such a bend allows the driver assembly 22400 to actuate the Tip Grasp 176 motion regardless of the relative positions of the base end housing 22100 and the operational end housing 22210. The path length 23400 may be kept constant using a variety of configurations. As shown in FIGS. 13-15, one exemplary configuration that keeps the path length constant is to construct the first pivotable section 22310 and the second pivotable section 22320 such that there is an opening 22330 large enough to allow the driver assembly 22400 to move laterally or to "bulge" out of the joint assembly 22300, as shown in FIG. 14, when the exemplary flexible wrist-type element 22000 exercises a Wrist Bend 174 motion (as shown in FIG. 4A and FIGS. 13-15).

3 Bar-Slider Wrist-Type Element

Figure 17:
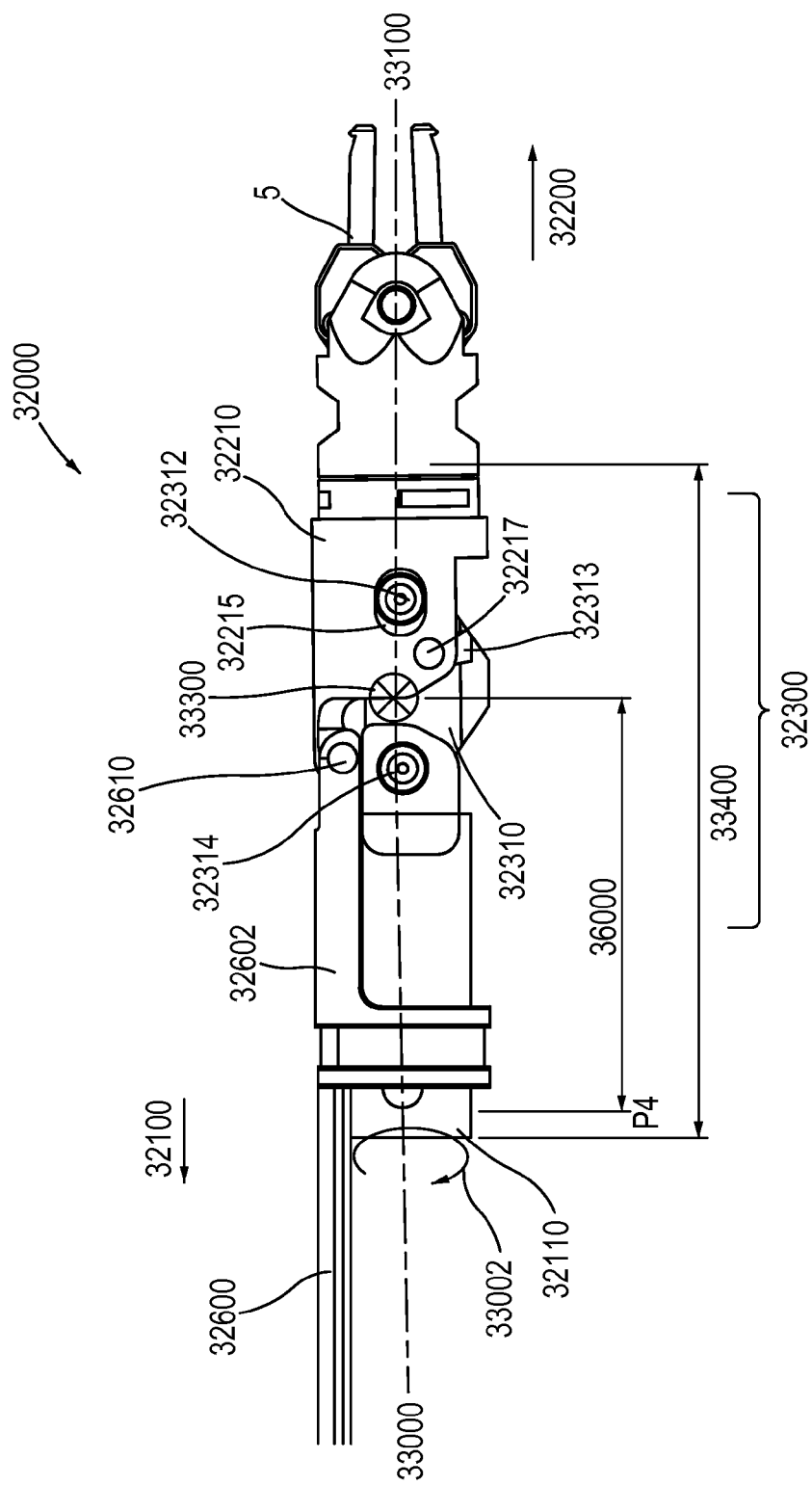
FIG. 17 is a side view of an end of an exemplary flexible wrist-type element that may be used in conjunction with the present invention in non-bending position.
Figure 18:
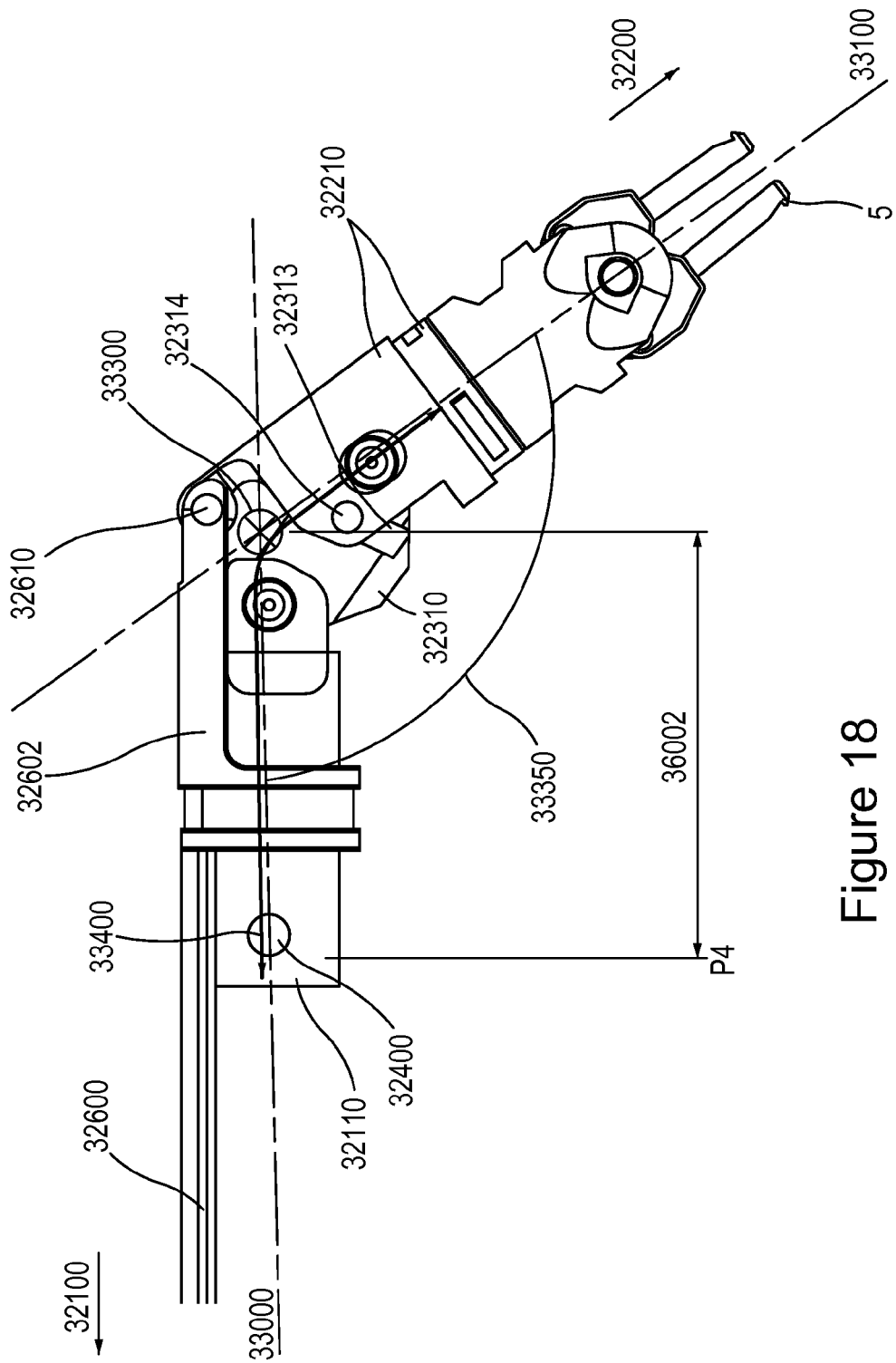
FIGS. 18 and 19 are side views of the base end 32100 and operational end 32200 illustrating relative motion during the course of operation.
Figure 19:
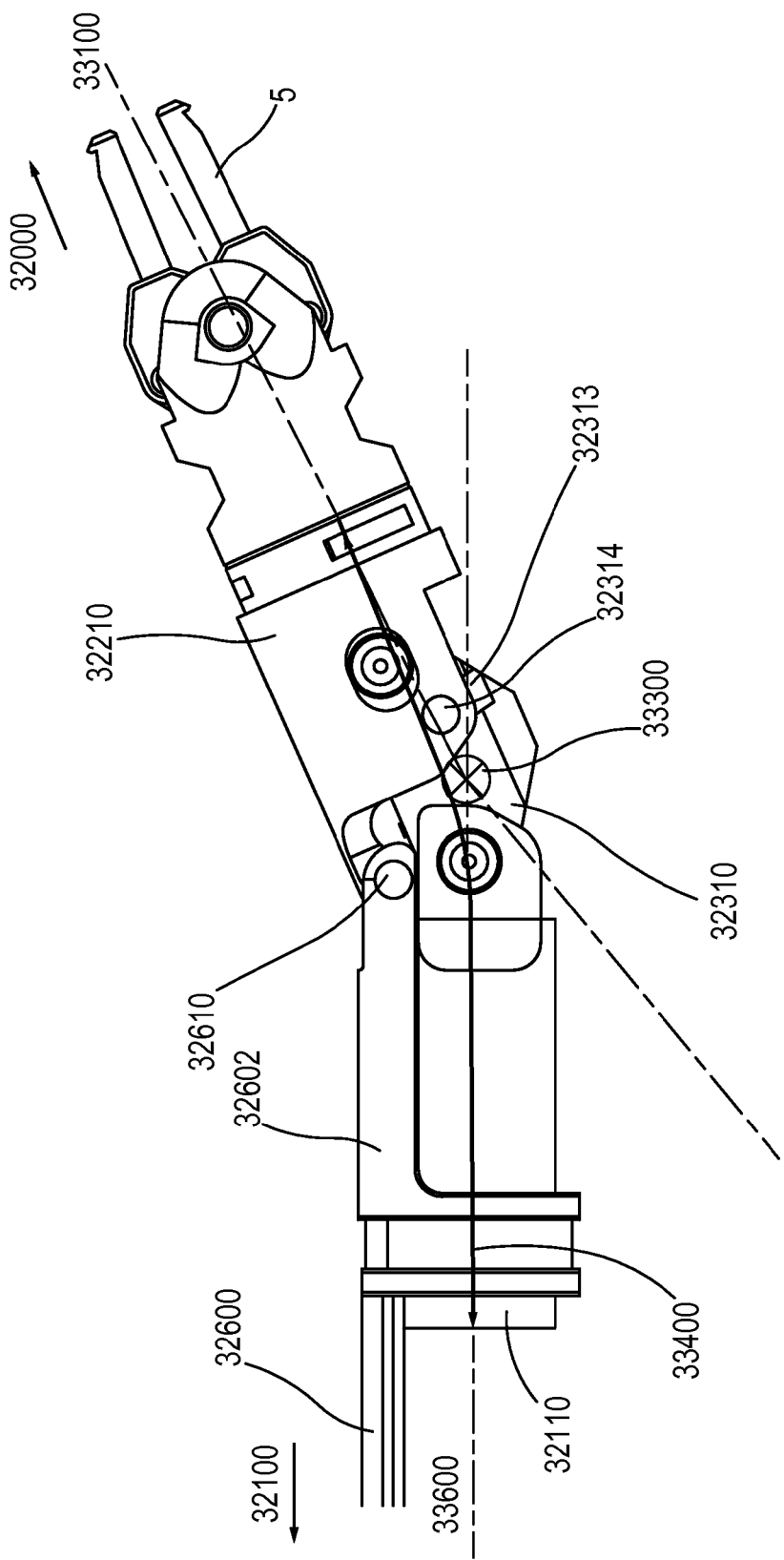
Figure 20:
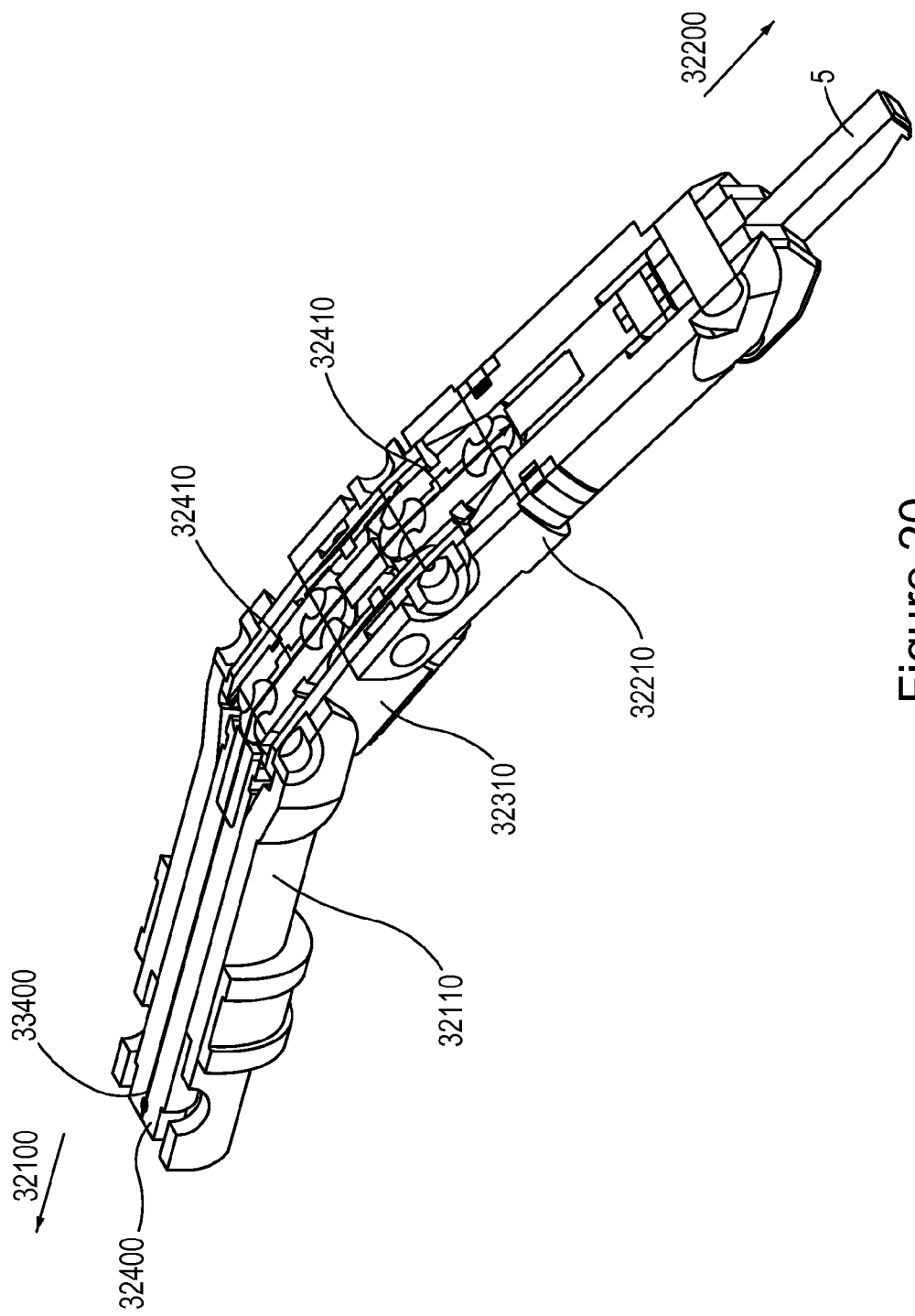
FIG. 20 is a cross-sectional view of the exemplary flexible wrist-type element of FIGS. 17-19 when it is bent.

FIG. 17 is a side view of an end of an exemplary flexible wrist-type element that may be used in conjunction with the present invention in non-bending position. FIGS. 18 and 19 are side views of the base end 32100 and operational end 32200 illustrating relative motion during the course of operation. FIG. 20 shows a cross-sectional view of the exemplary flexible wrist-type element of FIGS. 17-19 when it is bent. Such relative movement, as shown in FIGS. 18 and 19, may, for example, correspond to the Wrist Bend 174 motion shown in FIG. 4A.

As shown in FIG. 17, the exemplary flexible wrist-type element 32000 includes a base end 32100 and an operational end 32200 separated by joint assembly 32300. Generally the, base end 32100 includes a base housing 32110 and the operational end 32200 includes an operational end housing 32210. The base housing 32110 and the operational end housing 32210 may be of any suitable shape, including the shapes illustrated in FIG. 17. The base housing 32110 and the operational end housing 32210 may be monolithic, as shown in FIG. 17, or may contain any suitable number of subsidiary pieces, components and/or fixtures. A driver assembly 32400 extends from the base end 32100 to the operational end 32200 and generally allows one the remote actuation of an operational element, such as operational element 5 shown in FIG. 4A, at the operational end 32200 even when the axis meeting angle 33350 is nonzero.

More particularly, the base end 32100 of the exemplary flexible wrist-type element 32000 defines a first axis 33100 and the operational end 32200 defines a second axis 33200 that meet at a intersection point 33300. The intersection point 33300 may or may not be located on the joint assembly 32300. When the base end 32100 and operational end 32200 move relative to each other, as shown in FIGS. 17-19, the intersection point 33300 may move relative to one of, or both of, the operational end 32200 and the base end 32100. For example, FIG. 17 shows a distance 36000 between the intersection point 33300 and point P4 on the base end 32100. When the base end 32100 and operational end 32200 are moved relative to one another in a bending motion, as shown in FIG. 18, the distance between the intersection point 33300 and point P on the base end 32100 is increased to distance 36002. On the other hand, when the base end 32100 and operational end 32200 are moved relative to one another in another bending motion, as shown in FIG. 19, the distance between the intersection point 33300 and point P on the base end 32100 is decreased to distance 36002. These relative motions of the intersection point 33300 and components of the exemplary flexible wrist-type element 32000 are meant to be purely exemplary. Any other suitable relative motion of the intersection point 33300 with respect to the components of the exemplary flexible wrist-type element 32000 are included in the present invention. For example, the intersection point 33300 may move in substantially the opposite manner as shown in FIGS. 17-19. Alternatively, the intersection point 33300 may remain fixed with respect to components of the exemplary flexible wrist-type element 32000, or undergo motion along a complex curve.

The first axis 33100 and the second axis 33200 meet at the intersection point 33300 such that their intersection defines axis meeting angle 33350 (FIG. 18). The joint assembly 32300 can be used to move the base housing 32110 relative to the operational end housing 32210 such that the axis meeting angle 33350 the first axis 33100 and the second axis 33200 sweeps through a range of values. For example, the axis meeting angle 33350 may range in value from ±135°. Alternatively, in some embodiments, the axis meeting angle 33350 may range in value from as much as or more than ±90°. Although FIG. 17 shows a joint assembly 32300 that is restricted in motion such that the maximum negative value of the axis meeting angle 33350 is smaller than the maximum positive value of the axis meeting angle 33350, this is not necessarily the case. It is to be understood that the joint assembly 32300 can be constructed such that the maximum values of the axis meeting angle 33350 in both positive directions are equal, or that either one exceeds the other. The relative magnitude of the maximum values of the axis meeting angle 33350, in general, should depend on the particular application.

As shown in FIG. 17, the joint assembly 32300 includes a first pivotable section 32310. The inclusion of the first pivotable section 32310, base end housing 32110 and the operational end housing 32210 are the three elements that make up the "3 bar" linkage of the device. The first pivotable section 32310 may be of any suitable shape, including the shape illustrated in FIG. 17. The first pivotable section 32310 may be monolithic, as shown in FIG. 17, or may contain any suitable number of subsidiary pieces, components and/or fixtures. The first pivotable section 32310 may cooperate with the operational end housing 32210 and the base housing 32110 to move exemplary flexible wrist-type element 32000 through a range of motion. For example, the first pivotable section 32310 through axis meeting angle 33350 values, such as those shown in FIGS. 17-19. In addition, the first pivotable section 32310 may be configured to be capable of imparting other types of motion to the exemplary flexible wrist-type element 32000.

The first pivotable section 32310 may further be pivotably connected to the base end housing 32110 via a first base end pivot point 32314. The first pivotable section 32310 may further be pivotably connected to the operational end housing 32210 via a first operational end pivot point 32312. The first operational end pivot point 32312 is accommodated in the operational end housing 32210 by an enlarged point accommodator 32215 which allows lateral motion of the first operational end pivot point 32312 along the second longitudinal axis 33100, as shown in FIG. 17. Although only two pivot points are shown for the first pivotable section 32310 in FIG. 17, it is to be understood that the number of pivot points is not limited to that number. Any suitable number of pivot points is possible and additional pivot points may provide additional range of motion to the joint assembly 32300.

FIGS. 17 and 18 also show an input element 32600 that is pivotably coupled to the operational end housing 32210 via an input element sliding section 32602. Base housing 32110 further includes a track 32112 in which the Input element 32600 is slidably inserted such that it slides back and forth along the first longitudinal axis 33000 when actuated by, for example, the control portion 50. The first pivotable section 32310 is further pivotably coupled to the operational end housing 32210 via first operational end pivot point 32312. In addition, the first pivotable section 32310 includes a track 32313 that accommodates a pin 32217 of the operational end housing 32210. The track 32313 and pin 32217 are complementary to the first operational end pivot point 32312

Sweeping the axis meeting angle 33350 is accomplished using the various components of the joint assembly 32300. Sliding Input element 32600 along the first longitudinal axis 33000 causes the input element sliding section 32602 to push both the operational end housing 32210 via pivotable coupling 32610 such that the operational end housing 32210 pivots about operational end pivot point 32312 with respect to the first pivotable section 32310. Accordingly, the operational end housing 32210 may move laterally along second longitudinal axis 33100 in a manner subject to the constraints of the track 32112 and a track 32313. This further causes the operational end housing 32210 to pivot relative to the base end housing 32110 via first operational end pivot point 32312. This pivoting causes the operational end housing 32210, and therefore, to move relative to the base end housing 32110. Such motion of the operational end housing 32210 relative to the base end housing 32110 causes a relative movement of the first 33000 and second 33100 longitudinal axes sweeping through values of the axis meeting angle 33350 (e.g., as shown in FIG. 4C).

Generally, the driver assembly 32400 establishes a mechanical link between the base end 32100 and the operational end 32200. The driver assembly 32400 is best shown in FIG. 30. As discussed above, the operational end 32200 may include an operational element, such as, for example, the operational element 5 shown in FIG. 4A, that can be actuated by the driver assembly 32400. For example, control unit 3200 (FIG. 30) may be coupled to the driver assembly 32400 via hydraulic actuators in the manner described in the context of FIG. 4A. In such a configuration, a user's motions while operating the control 32000 may be transferred hydraulically, for example, to the driver assembly 32400. The driver assembly 32400, then, may transfer the same motions (or amplified version of such motions) mechanically to the operational element 5. In this way the driver assembly 32400 may act as a mechanical conduit between the control assembly 3200 and the operational element 5. Such a configuration may be used to perform each of the micro motions shown in FIG. 4A. For example, actuation of the control unit 3200 may cause the driver assembly 32400 to cause the operational element 5 to perform one or more of the Tip Grasp 176, Tip Rotation 175, Wrist Bend 174 or Forearm Rotation 173 motions shown in FIG. 4A.

The driver assembly 32400 may, for example, be able to transfer mechanical motion to, actuate or mechanically communicate with the operational element 5 such that the operational element 5 can, for example, perform some or all of the micro motions shown in FIG. 4A. For example, the Tip Grasp 176 motion may be actuated by moving the driver assembly 32400 along direction 33001, a direction that is co-incident and co-linear with the path length 33400 made by the driver assembly 32400 throughout the exemplary flexible wrist-type element 32000. The Tip Rotation 175 motion, for example, may be actuated by rotating the driver assembly 32400 along rotational direction 33002 with respect to the base end housing 32110 and the operational end housing 32210.

The driver assembly 32400 may include, for example, one or more u-joints 32410, as shown in FIGS. 5 and 36 in order to, among other things, transfer mechanical motion to, actuate or mechanically communicate with the operational element 5. U-joints 32410 may, for example, be similar to the U-joint 95 shown in FIG. 4D. The u-joints 32410 may allow the driver assembly 32400 to maintain mechanical communication between a base end section 32420 and an operational end section 32430 of the driver assembly 32400 even as the exemplary flexible wrist-type element 32000 is bent, as shown, for example, in FIG. 18. Maintaining mechanical communication in this way enables the driver assembly 32400 to actuate the operational element 5 in the manner described above even when the joint assembly 32300 is bent a Wrist Bend 174 motion, as shown, for example, in FIG. 18. The driver assembly 32400 could also or alternatively be fashioned from other flexible mechanical devices such as, for example, push-pull cables or other cables. This wrist structure, and any of the wrist structures discussed herein could be used to maintain even path length for non-driving elements, such as wires, hoses, etc.

Generally the joint assembly 32300 is constructed so that the path length 33400 remains substantially constant during a Wrist Bend 174 (FIG. 4A, FIGS. 17-19). Keeping the path length 33400 constant during such a bend allows the driver assembly 32400 to actuate the Tip Grasp 176 motion regardless of the relative positions of the base end housing 32100 and the operational end housing 32210. The path length 33400 may be kept constant using a variety of configurations. As shown in FIGS. 17-19, one exemplary configuration that keeps the path length constant is to construct the first pivotable section 32310 and the second pivotable section 32320 such that there is an opening 32330 large enough to allow the driver assembly 32400 to move laterally or to "bulge" out of the joint assembly 32300, as shown in FIG. 18, when the exemplary flexible wrist-type element 32000 exercises a Wrist Bend 174 motion (as shown in FIG. 4A and FIGS. 17-19).

Figure 21:
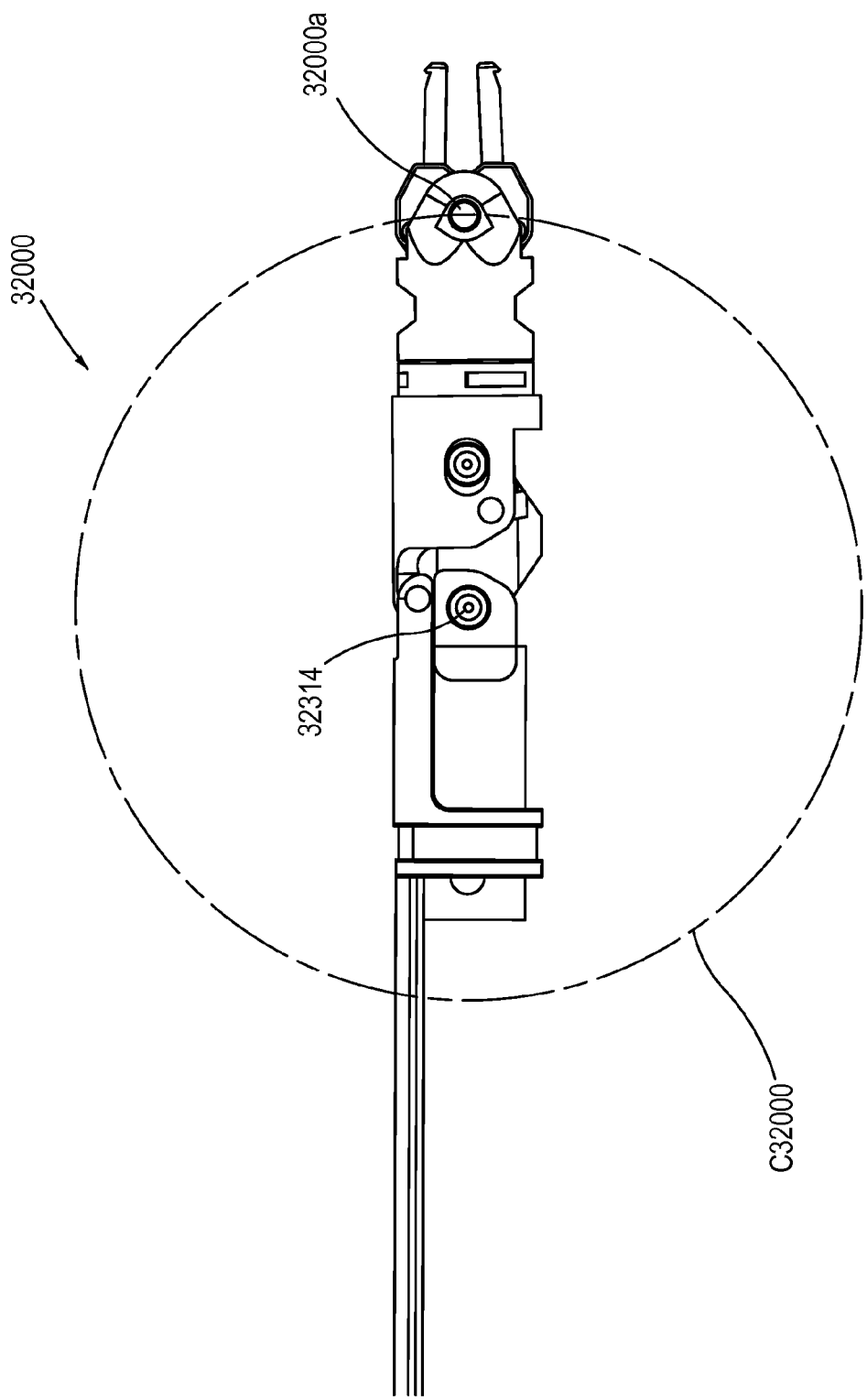
FIG. 21 is a side view of an end of the exemplary flexible wrist-type element of FIGS. 17-19 in a first position.
Figure 22:
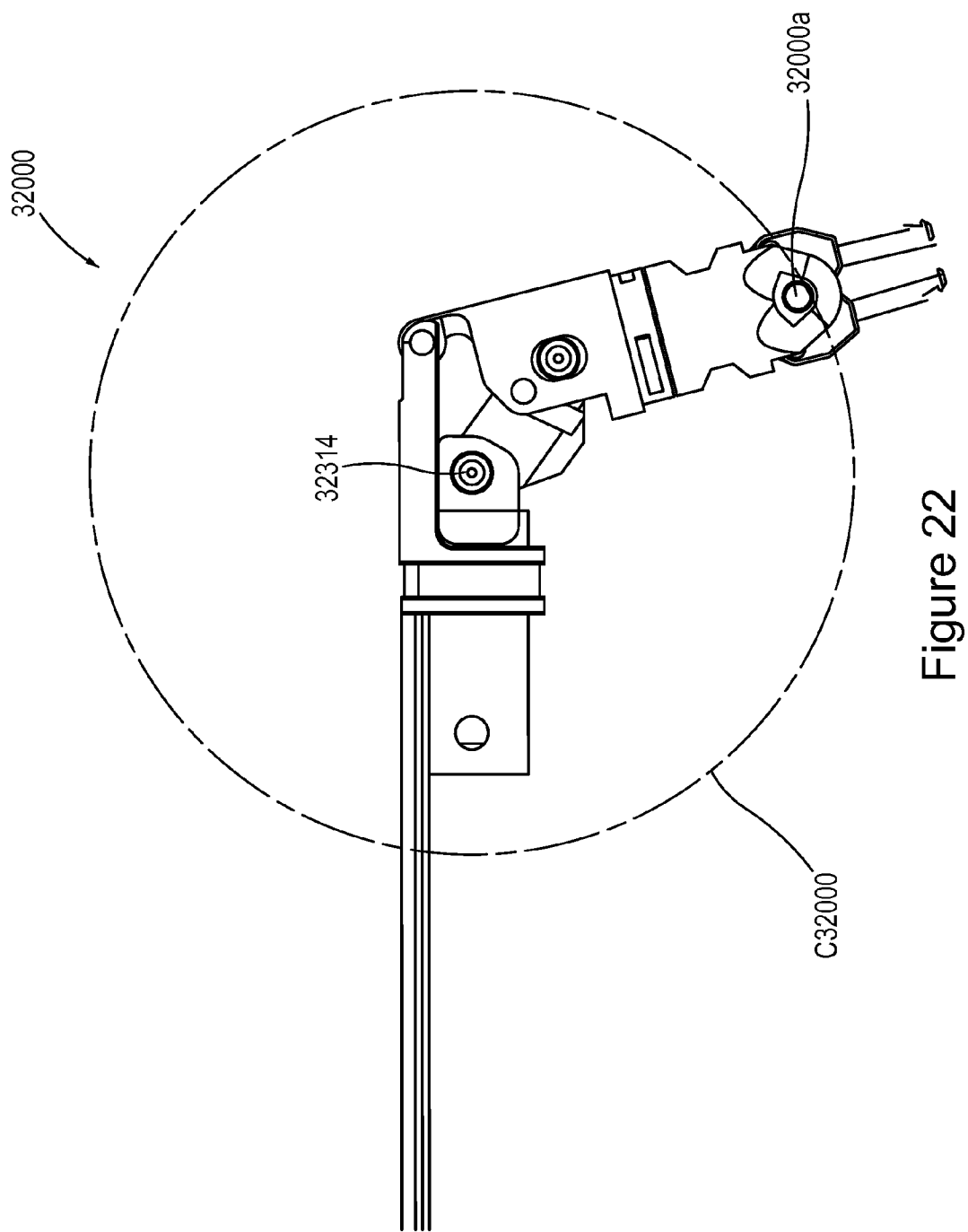
FIG. 22 is a side view of an end of the exemplary flexible wrist-type element of FIGS. 17-19 in a second position.
Figure 23:
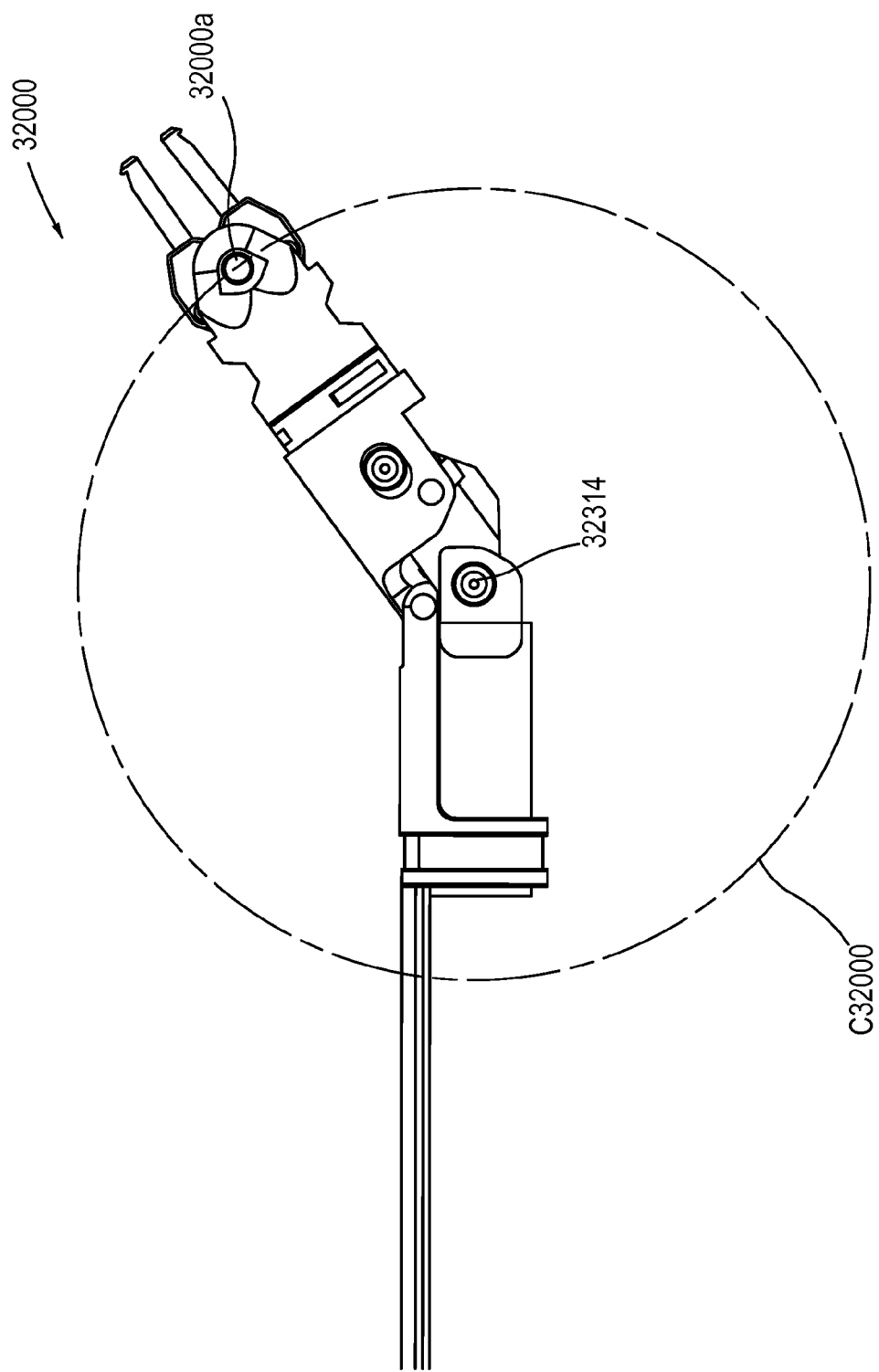
FIG. 23 is a side view of an end of the exemplary flexible wrist-type element of FIGS. 17-19 in a third position.

FIGS. 21-23 show side views of an end of the exemplary flexible wrist-type element of FIG. 17, shown in three different positions to illustrate that portions of the flexible wrist-type element undergo a complex motion (e.g., a complex curve) upon bend. FIGS. 21-23 show, in particular, the motion of point 32000A relative to concentric circle C32000 centered on first base end pivot point 32314. Complex curve C32001 shows the curve defining the actual motion of point 32000A. The choice of the point 32000A is merely illustrated, and, many other exemplary points on exemplary flexible wrist-type element 32000 may be used to similarly illustrate complex motion.

In FIG. 21, point 32000A is shown as aligned with concentric circle C2001. When the exemplary flexible wrist-type element 32000 is moved to the position shown in FIG. 22, however, point 32000A has moved along complex curve C32001 to become unaligned, as shown, with concentric circle C2001. When the exemplary flexible wrist-type element 32000 is moved to the position shown in FIG. 23, point 32000A has moved along complex curve C32001 to become unaligned, as shown, with concentric circle C2001. In other words, the motion of point 32000A, as well as other portions of exemplary flexible wrist-type element 32000, does not correspond to a pivot about a pivot point as shown in the related art. This motion can be directly contrasted with that shown for the pivot system C32000a of the related in FIGS. 6E-6G and discussed above, for example.

Although the invention has been described with reference to various aspects of the present invention and examples with respect to a surgical instrument, it is within the scope and spirit of the invention to incorporate or use with any suitable mechanical device. Further, while the invention has been described with reference to a surgeon, the invention may be used with multiple users, depending on circumstances in which the invention is used. Thus, it should be understood that numerous and various modifications may be made without departing from the spirit of the invention.

What is claimed is:

1. A flexible wrist-type element, comprising:
a base housing extending along a first longitudinal axis and having a base end;
an operational housing extending along a second longitudinal axis and having an operational end, the operational end being opposite the base end;
an operational element moveably connected to the operational housing at the operational end;
a joint assembly between the base end and the operational end, the joint assembly movably connecting the base housing and the operational housing;
wherein the joint assembly allows relative movement of the operational housing and the base housing between a first position and a second position, wherein a point of intersection between the second longitudinal axis and the first longitudinal axis moves during movement between the first position and the second position such that a first distance between the point of intersection and a point on the base housing in the first position is different than a second distance between the point of intersection and the point on the base housing in the second position; and
a driver assembly moveably supported by the base housing and the operational housing, wherein the driver assembly is configured to actuate the operational element relative to the operational housing, wherein the driver assembly defines a path length between the base end and the operational end and the path length remains substantially constant as an angle between the first longitudinal axis and the second longitudinal axis is varied.

2. The flexible wrist-type element of claim 1, further including:
a first point on the operational housing configured such that, when an angle between the first longitudinal axis and the second longitudinal axis is varied, the first point on the operational housing traces a first curve;
a second point on the operational housing configured such that, when the angle between the first longitudinal axis and the second longitudinal axis is varied, the second point on the operational housing traces a second curve, and
wherein the first and second curves differ.

3. The flexible wrist-type element of claim 1, wherein the operational end pivots with respect to the base end via multiple pivot points.

4. The flexible wrist-type element of claim 1, further including:
an input element; and
wherein the input element, the joint assembly and the operating end housing are connected via a four bar linkage.

5. The flexible wrist-type element of claim 1, further including:
an input element; and
wherein the input element, the joint assembly and the operating end housing are connected via a three bar linkage.

6. A flexible wrist-type element, comprising:
a base housing extending along a first longitudinal axis and having a base end;
an operational housing extending along a second longitudinal axis and having an operational end, the operational end being opposite the base end;
an operational element moveably connected to the operational housing at the operational end;
a joint assembly between the base end and the operational end, the joint assembly movably connecting the base housing and the operational housing;
wherein the joint assembly allows relative movement of the operational housing and the base housing between a first position and a second position;
a driver assembly moveably supported by the base housing and the operational housing;
wherein the driver assembly is configured to actuate the operational element relative to the operational housing when an angle between the first longitudinal axis and the second longitudinal axis assumes a value;
a first point on the operational housing configured such that, when the angle between the first longitudinal axis and the second longitudinal axis is varied, the first point on the operational housing traces a first curve;
a second point on the operational housing configured such that, when the angle between the first longitudinal axis and the second longitudinal axis is varied, the second point on the operational housing traces a second curve; and
wherein the driver assembly defines a path length between the base end and the operational end, and the path length remains constant as the angle between the first longitudinal axis and the second longitudinal axis is varied.

7. The flexible wrist-type element of claim 6, wherein the joint assembly allows relative movement of the operational housing and the base housing between the first position and the second position, wherein a point of intersection between the second longitudinal axis and the first longitudinal axis moves during movement between the first position and the second position and wherein the first and second curves differ.

8. The flexible wrist-type element of claim 6, wherein the operational end pivots with respect to the base end via multiple pivot points.

9. The flexible wrist-type element of claim 6, further including:
an input element; and
wherein the input element, the joint assembly and the operating end housing are connected via a four bar linkage.

10. The flexible wrist-type element of claim 6, further including:
an input element; and
wherein the input element, the joint assembly and the operating end housing are connected via a three bar linkage.

11. A flexible wrist-type element, comprising:
a base housing extending along a first longitudinal axis and having a base end;
an operational housing extending along a second longitudinal axis and having an operational end, the operational end being opposite the base end;
an operational element moveably connected to the operational housing at the operational end;

a joint assembly between the base end and the operational end, the joint assembly movably connecting the base housing and the operational housing;
wherein the joint assembly allows relative movement of the operational housing and the base housing between a first position and a second position;
a driver assembly moveably supported by the base housing and the operational housing;
wherein the driver assembly is configured to actuate the operational element relative to the operational housing when an angle between the first longitudinal axis and the second longitudinal axis assumes a value;
wherein the operational end pivots with respect to the base end via multiple pivot points; and
wherein the driver assembly defines a path length between the base end and the operational end, and the path length remains constant as the angle between the first longitudinal axis and the second longitudinal axis is varied.

12. The flexible wrist-type element of claim 11, wherein the joint assembly allows relative movement of the operational housing and the base housing between the first position and the second position, wherein a point of intersection between the second longitudinal axis and the first longitudinal axis moves during movement between the first position and the second position.

13. The flexible wrist-type element of claim 11, further including:
a first point on the operational housing configured such that, when the angle between the first longitudinal axis and the second longitudinal axis is varied, the first point on the operational housing traces a first curve;
a second point on the operational housing configured such that, when the angle between the first longitudinal axis and the second longitudinal axis is varied, the second point on the operational housing traces a second curve, and
wherein the first and second curves differ.

14. The flexible wrist-type element of claim 11, further including:
an input element; and
wherein the input element, the joint assembly and the operating end housing are connected via a four bar linkage.

15. The flexible wrist-type element of claim 1, further including:
an input element; and
wherein the input element, the joint assembly and the operating end housing are connected via a three bar linkage.

16. A flexible wrist-type element, comprising:
a base housing extending along a first longitudinal axis and having a base end;
an operational housing extending along a second longitudinal axis and having an operational end, the operational end being opposite the base end;
an operational element moveably connected to the operational housing at the operational end;
a joint assembly between the base end and the operational end, the joint assembly movably connecting the base housing and the operational housing;
wherein the joint assembly allows relative movement of the operational housing and the base housing between a first position and a second position; and
a driver assembly moveably supported by the base housing and the operational housing;
wherein the driver assembly is configured to actuate the operational element relative to the operational housing; and
wherein the driver assembly defines a path length between the base end and the operational end and the path length remains substantially constant as an angle between the first longitudinal axis and the second longitudinal axis is varied.

17. The flexible wrist-type element of claim 16, wherein the joint assembly allows relative movement of the operational housing and the base housing between a first position and a second position, wherein a point of intersection between the second longitudinal axis and the first longitudinal axis moves during movement between the first position and the second position.

18. The flexible wrist-type element of claim 16, further including:
a first point on the operational housing configured such that, when the angle between the first longitudinal axis and the second longitudinal axis is varied, the first point on the operational housing traces a first curve;
a second point on the operational housing configured such that, when the angle between the first longitudinal axis and the second longitudinal axis is varied, the second point on the operational housing traces a second curve, and
wherein the first and second curves differ.

19. The flexible wrist-type element of claim 16, wherein the operational end pivots with respect to the base end via multiple pivot points.

20. The flexible wrist-type element of claim 16, further including:
an input element; and
wherein the input element, the joint assembly and the operating end housing are connected via a four bar linkage.

21. The flexible wrist-type element of claim 16, further including:
an input element; and
wherein the input element, the joint assembly and the operating end housing are connected via a three bar linkage.

22. A flexible wrist-type element, comprising:
a base housing extending along a first longitudinal axis and having a base end;
an operational housing extending along a second longitudinal axis and having an operational end, the operational end being opposite the base end;
an operational element moveably connected to the operational housing at the operational end;
a joint assembly between the base end and the operational end, the joint assembly movably connecting the base housing and the operational housing;
wherein the joint assembly allows relative movement of the operational housing and the base housing between a first position and a second position; a driver assembly moveably supported by the base housing and the operational housing;
wherein the driver assembly is configured to actuate the operational element relative to the operational housing;
an input element;
wherein the input element, the joint assembly and the operating end housing are connected via a four bar linkage; and
wherein the driver assembly defines a path length between the base end and the operational end, and the path length remains substantially constant as an angle between the first longitudinal axis and the second longitudinal axis is varied.

23. The flexible wrist-type element of claim 22, wherein the joint assembly allows relative movement of the operational housing and the base housing between the first position and the second position, wherein a point of intersection between the second longitudinal axis and the first longitudinal axis moves during movement between the first position and the second position.

24. The flexible wrist-type element of claim 22, further including:
    a first point on the operational housing configured such that, when an angle between the first longitudinal axis and the second longitudinal axis is varied, the first point on the operational housing traces a first curve;
    a second point on the operational housing configured such that, when the angle between the first longitudinal axis and the second longitudinal axis is varied, the second point on the operational housing traces a second curve, and
    wherein the first and second curves differ.

25. The flexible wrist-type element of claim 22, wherein the operational end pivots with respect to the base end via multiple pivot points.

26. The flexible wrist-type element of claim 22, further including:
    an input element; and
    wherein the input element, the joint assembly and the operating end housing are connected via a three bar linkage.

27. A flexible wrist-type element, comprising:
    a base housing extending along a first longitudinal axis towards a base end;
    an operational housing extending along a second longitudinal axis towards an operational end;
    an operational element moveably connected to the operational housing;
    a joint assembly movably connecting the base housing and the operational housing;
    wherein the joint assembly allows relative movement of the operational housing and the base housing between a first position and a second position;
    a driver assembly moveably supported by the base housing and the operational housing;
    wherein the driver assembly is configured to actuate the operational element relative to the operational housing;
    an input element; and
    wherein the input element, the joint assembly and the operating end housing are connected via a three bar linkage.

* * * * *